(12) United States Patent
Boch

(10) Patent No.: US 10,736,865 B2
(45) Date of Patent: *Aug. 11, 2020

(54) PHARMACEUTICAL FORMULATIONS COMPRISING 9-CIS-RETINYL ESTERS IN A LIPID VEHICLE

(71) Applicant: RETINAGENIX THERAPEUTICS, INC., Palo Alto, CA (US)

(72) Inventor: Ronald Erwin Boch, North Vancouver (CA)

(73) Assignee: RETINAGENIX THERAPEUTICS, INC., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/158,738

(22) Filed: Oct. 12, 2018

(65) Prior Publication Data

US 2019/0183835 A1 Jun. 20, 2019

Related U.S. Application Data

(60) Continuation of application No. 15/274,257, filed on Sep. 23, 2016, now Pat. No. 10,130,606, which is a division of application No. 13/496,113, filed as application No. PCT/US2009/059126 on Sep. 30, 2009, now abandoned.

(60) Provisional application No. 61/242,741, filed on Sep. 15, 2009.

(51) Int. Cl.
| | | |
|---|---|---|
| *A61K 31/22* | (2006.01) | |
| *A61K 31/44* | (2006.01) | |
| *A61K 9/00* | (2006.01) | |
| *A61K 9/08* | (2006.01) | |
| *A61K 31/07* | (2006.01) | |
| *A61K 47/44* | (2017.01) | |
| *A61K 9/107* | (2006.01) | |
| *A61K 47/08* | (2006.01) | |

(52) U.S. Cl.
CPC ............ *A61K 31/22* (2013.01); *A61K 9/0019* (2013.01); *A61K 9/0095* (2013.01); *A61K 9/08* (2013.01); *A61K 9/107* (2013.01); *A61K 31/07* (2013.01); *A61K 47/08* (2013.01); *A61K 47/44* (2013.01)

(58) Field of Classification Search
CPC .... A61K 31/22; A61K 9/0019; A61K 9/0095; A61K 9/08; A61K 31/07; A61K 47/44; A61K 9/107; A61K 47/04
See application file for complete search history.

(56) References Cited

U.S. PATENT DOCUMENTS

| | | | |
|---|---|---|---|
| 3,196,078 A | 7/1965 | Chatzinoff et al. | |
| 3,517,067 A | 6/1970 | Stern | |
| 4,022,913 A * | 5/1977 | Newmark | A61K 9/0019 514/546 |
| 4,532,133 A * | 7/1985 | Schmidt | A61K 31/07 514/725 |
| 5,457,135 A | 10/1995 | Baranowitz et al. | |
| 5,620,970 A | 4/1997 | Han et al. | |
| 5,744,148 A * | 4/1998 | Habif | A61K 8/062 424/401 |
| 5,837,728 A | 11/1998 | Purcell | |
| 5,869,468 A | 2/1999 | Freeman | |
| 6,300,328 B1 | 10/2001 | Klimko | |
| 6,552,009 B2 | 4/2003 | Achkar | |
| 6,696,069 B2 | 2/2004 | Harichian et al. | |
| 7,494,222 B2 | 2/2009 | Jackson et al. | |
| 7,798,646 B2 | 9/2010 | Jackson et al. | |
| 7,951,841 B2 | 5/2011 | Palczewski et al. | |
| 8,324,270 B2 | 12/2012 | Maeda et al. | |
| 8,962,691 B2 | 2/2015 | Palczewski et al. | |
| 9,173,856 B2 | 11/2015 | Strong et al. | |
| 10,130,606 B2 * | 11/2018 | Boch | A61K 9/0019 |
| 2002/0028849 A1 | 3/2002 | Godkin et al. | |
| 2002/0142016 A1 * | 10/2002 | Granger | A61K 8/02 424/401 |
| 2003/0215413 A1 | 11/2003 | Fares et al. | |
| 2003/0228277 A1 | 12/2003 | Gehlsen | |
| 2004/0022766 A1 | 2/2004 | Acland et al. | |
| 2004/0077604 A1 | 4/2004 | Lichtenberger | |
| 2004/0097587 A1 | 5/2004 | Arbiser | |
| 2004/0242704 A1 | 12/2004 | Palczewski et al. | |
| 2005/0042278 A1 | 2/2005 | Ditzinger et al. | |
| 2005/0159662 A1 | 7/2005 | Imanishi et al. | |
| 2006/0167088 A1 | 7/2006 | Widder et al. | |
| 2006/0177392 A1 | 8/2006 | Walden | |
| 2006/0240098 A1 | 10/2006 | Castor | |
| 2006/0281821 A1 | 12/2006 | Palczewski et al. | |
| 2007/0071872 A1 | 3/2007 | Goeseels et al. | |
| 2008/0221208 A1 | 9/2008 | Palczewski et al. | |

(Continued)

FOREIGN PATENT DOCUMENTS

| | | | |
|---|---|---|---|
| CA | 2601278 A1 | 9/2005 | |
| CA | 2714530 A1 | 8/2009 | |

(Continued)

OTHER PUBLICATIONS

Palczewski K, G-Protein-coupled Receptor Rhodopsln, Annual Review of Biochemistry, 2006, vol. 75, p. 743-767.

(Continued)

*Primary Examiner* — Shirley V Gembeh

(74) *Attorney, Agent, or Firm* — Mintz Levin Cohn Ferris Glovsky and Popeo PC

(57) ABSTRACT

Pharmaceutical formulations comprising 9-cis-retinyl esters in a lipid vehicle are described as retinoid replacement therapies for treating retinal degenerations in humans.

20 Claims, 22 Drawing Sheets

(56) References Cited

U.S. PATENT DOCUMENTS

| | | |
|---|---|---|
| 2008/0275133 A1 | 11/2008 | Schwartz et al. |
| 2009/0286808 A1* | 11/2009 | Kaushal .............. A61K 31/415 514/255.02 |
| 2010/0010084 A1 | 1/2010 | Yu |
| 2010/0035986 A1 | 2/2010 | Maeda et al. |
| 2010/0136108 A1 | 6/2010 | Ditzinger et al. |
| 2011/0034554 A1 | 2/2011 | Washington |
| 2011/0257266 A1 | 10/2011 | Strong et al. |
| 2011/0288170 A1 | 11/2011 | Palczewski et al. |
| 2012/0041073 A1 | 2/2012 | Palczewski et al. |
| 2012/0178806 A1 | 7/2012 | Boch |
| 2012/0322891 A1 | 12/2012 | Palczewski et al. |
| 2013/0072443 A1 | 3/2013 | Palczewski et al. |
| 2013/0072556 A1 | 3/2013 | Palczewski et al. |
| 2013/0072557 A1 | 3/2013 | Maeda et al. |
| 2013/0072558 A1 | 3/2013 | Maeda et al. |
| 2013/0072559 A1 | 3/2013 | Palczewski et al. |
| 2013/0072560 A1 | 3/2013 | Palczewski et al. |
| 2013/0072561 A1 | 3/2013 | Maeda et al. |
| 2013/0072569 A1 | 3/2013 | Palczewski et al. |
| 2013/0079403 A1 | 3/2013 | Palczewski et al. |
| 2013/0196950 A1 | 8/2013 | Palczewski et al. |

FOREIGN PATENT DOCUMENTS

| | | |
|---|---|---|
| CN | 1169854 A | 1/1998 |
| CN | 1455780 A | 11/2003 |
| EP | 184942 B1 | 8/1990 |
| EP | 0803248 A2 | 10/1997 |
| EP | 552624 B1 | 6/2000 |
| GB | 1449027 A | 9/1976 |
| GB | 1452012 A | 10/1976 |
| GB | 1526410 A | 9/1978 |
| JP | S61-275266 | 12/1986 |
| JP | H06340525 | 12/1994 |
| JP | 8198746 | 8/1996 |
| JP | 2003-292414 A | 10/2003 |
| RU | 2106843 C1 | 3/1998 |
| WO | WO-1996/024344 A1 | 8/1996 |
| WO | WO-1997003655 A1 | 2/1997 |
| WO | WO-1999/009969 A1 | 3/1999 |
| WO | WO-1999020265 A1 | 4/1999 |
| WO | WO-1999/029315 A1 | 6/1999 |
| WO | WO-2000/068364 | 11/2000 |
| WO | WO-2002/055540 | 1/2001 |
| WO | WO-2001001960 A1 | 1/2001 |
| WO | WO2011034551 A2 | 3/2001 |
| WO | WO-2002/082904 | 10/2002 |
| WO | WO-2003039521 A1 | 5/2003 |
| WO | WO-2003045379 A1 | 6/2003 |
| WO | WO-2003/059336 | 7/2003 |
| WO | WO-2004082622 A2 | 9/2004 |
| WO | WO-2005048994 A1 | 6/2005 |
| WO | WO-2005/079774 A2 | 9/2005 |
| WO | WO-2006002097 A2 | 1/2006 |
| WO | WO-2006/033734 A2 | 3/2006 |
| WO | WO-2007056242 A1 | 5/2007 |
| WO | WO-2007092509 A2 | 8/2007 |
| WO | WO-2009102418 A1 | 8/2009 |
| WO | WO-2011034551 A2 | 3/2011 |
| WO | WO-2011132084 A2 | 10/2011 |

OTHER PUBLICATIONS

Ridge, K., et al, Visual rhodopsin sees the light: Structure and mechanism of G protein signaling, J Biol Chem, 2007, vol. 282, No. 31, p. 9297-9301.

Travis, GH., et al, Diseases caused by defects in the visual cycle: retinoids as potential therapeutic agents, Annu Rev Pharmacol Toxicol, 2007, vol. 47, p. 469-512.

Gu, S.M., et al., Mutations in RPE65 cause autosomal recessive childhood-onset severe retinal dystrophy, Nature Genetics, 1997, vol. 17, No. 2, p. 194-197.

Perrault, I., et al., Leber congenital amaurosis, Mol Genet Metab, 1999, vol. 68, No. 2, p. 200-208.

Fazzi, E., et al., Leber's congenital amaurosis: an update, Eur J Paediatr Neurol, 2003, vol. 7, No. 1, p. 13-22.

Fazzi, E., et al., Response to pain in a group of healthy term newborns: behavioral and physiological aspects, Functional Neurology, 1996, vol. 11, No. 1, p. 35-43.

Hamel, C.P., et al., Molecular cloning and expression of RPE65, a novel retinal pigment epithelium-specific microsomal protein that is post-transciptionally regulated in vitro, J Biol Chem, 1993, vol. 268, No. 21, p. 15751-15757.

Jin, M., et al., RPE65 is the retinoid isomerase in bovine retinal pigment epithelium, Cell, 2005, vol. 122, No. 3, p. 449-459.

Moiseyev, G., et al., RPE65 is the isomerohydrolase in the retinoid visual cycle, Proceedings of the National Academy of Sciences, 2005, vol. 102, No. 35, p. 12413-12418.

Redmond, T.M., et al., Mutation of key residues of RPE65 abolishes its enzymatic role as isomerohydrolase in the visual cycle, Proceedings of the National Academy of Sciences, 2005, vol. 102, No. 38, p. 13658-13663.

Marlhens, F., et al., Mutations in RPE65 cause Leber's congenital amaurosis, Nature Genetics, 1997, vol. 17, No. 2, p. 139-14.

Morimura, H., et al., Mutations in the RPE65 gene in patients with autosomal recessive retinitis pigmentosa or leber congenital amaurosis, Proceedings of the National Academy of Sciences, 1998, vol. 95, No , p. 3088-3093.

Thompson, D.A., et al., Genetics and phenotypes of RPE65 mutations in inherited retinal degeneration, Investigative Ophthalmology & Visual Science, 2000, vol. 41, No. 13, p. 4293-4299.

Lorenz, B., et al., Early-onset severe rod-cone dystrophy in young children with RPE65 mutations, Investigative Ophthalmology & Visual Science, 2000, vol. 41, No. 9, p. 2735-2742.

Redmond, T.M., et al., RPE65 is necessary for production of 11-cis-vitamin A in the retinal visual cycle, Nature Genetics, 1998, vol. 20, No. 4, p. 344-351.

Pang, J.J., et al., Retinal degeneration 12 (rd12): a new, spontaneously arising mouse model for human Leber congenital amaurosis (LCA), Molecular Vision, 2005, vol. 11, p. 152-162.

Wrigstad, A., et al., Ultrastructural changes of the retina and the retinal pigment epithelium in Briard dogs with hereditary congenital night blindness and partial day blindness, Experimental Eye Research, 1992, vol. 55, No. 6, 805-818.

Acland, G.M., et al., Gene therapy restores vision in a canine model of childhood blindness, Nature genetics, 2001, vol. 28, No. 1, p. 92-95.

Imanishi, Y., et al., Noninvasive two-photon imaging reveals retinyl ester storage structures in the eye, Journal of Cell Biology, 2004, vol. 164, No. 3, p. 373-383.

Bainbridge, J.W., et al., Effect of gene therapy on visual function in Leber's congenital amaurosis, New England J Med, 2008, vol. 358, No. 21, p. 2231-2239.

Maguire, A.M., et al., Safety and efficacy of gene transfer for Leber's congenital amaurosis, New England J Med, 2008, vol. 358, No. 21, p. 2240-2248.

Yanai, D., et al., Visual performance using a retinal prosthesis in three subjects with retinitis pigmentosa, Am J Opthal, 2007, vol. 143, No. 5, p. 820-827.

Van Hooser, J.P., et al., Rapid restoration of visual pigment and function with oral retinoid in a mouse model of childhood blindness, Proceedings of the National Academy of Sciences, 2000, vol. 97, No. 15, p. 8623-8628.

Van Hooser, J.P., et al., Recovery of visual functions in a mouse model of Leber congenital amaurosis, J Biol Chem, 2002, vol. 277, No. 21, p. 19173-19182.

Aleman, T.S., et al., Impairment of the transient pupillary light reflex in RPE65(−/−) mice and humans with leber congenital amaurosis, Investigative Ophthalmology & Visual Science, 2004, vol. 45, No. 4, p. 1259-1271.

Batten, M.L., et al., Pharmacological and rAAV gene theratpy rescue of visual functions in a blind mouse model of Leber congenital amaurosis, PLoS Med, 2005, vol. 2, No. 11, p. e333.

(56) References Cited

OTHER PUBLICATIONS

Maeda, A., et al., Role of photoreceptor-specific retinol dehyrogenase in the retinoid cycle in vivo, J Biol Chem, 2005, vol. 280, No. 19, p. 18822-18832.
Maeda T., et al., a critical role of CaBP4 in the cone synapse, Investigative Ophthalmology & Visual Science, 2005, vol. 46, No. 11, p. 4320-4327.
Scholl, et al., Safety and Proof-of-Concept Study of Oral QLT091001 in Retinitis Pigmentosa Due to Inherited Deficiencies of Retinal Pigment Epithelial 65 Protein (RPE65) or Lecithin; Retinol Acyltransferase (LRAT), PLOS One.; 10(12); e0143846; vol. 10(12) (2015).
U.S. Appl. No. 14/875,342, filed Oct. 5, 2015, Strong et al.
U.S. Appl. No. 15/096,048, filed Apr. 11, 2018, Cadden.
Ablonczy et al., "11-cis-retinyl reduces constitutive opsin phosphorylyzation and improves quantum catch in retinoid-deficient mouse rod photoreceptors", J. Biol. Chem., vol. 277, pp. 40491-40498 (2002).
Accutane Label, NDA 18-662/S-056, pp. 11-55 (2005).
Acland et al., "Long-term restoration of rod and cone vision by single dose rAAV-mediated gene transfer to the retina in a canine model of childhood blindness", Mol. Ther., vol. 12, No. 6, pp. 1072-1082 (2005).
Acland GM, et al. Gene therapy restores vision in a canine model of childhood blindness. Nature Genetics 2001; 28:92-95.
Aggarwal et al., "2-Halogeno-1,3-dithiane 1,3-dioxide: a diastereoselective carbonyl anion equivalent in reactions with aldehydes", J. Chem. Soc., vol. 1, pp. 11-19 (1997).
Albeck et al., "Factors affecting the absorption maxima of acidic forms of bacteriorhodopsin; A study with artificial pigments" Biophys. J. 56:1259-65 (1989).
Aleman TS, et al, "Impairment of the transient pupillary light reflex in Rpe65(−/−) mice and humans with leber congenital amaurosis," Investigative Ophthalmology & Visual Science, 45(4):1259-1271 (2004).
Allen LH "Estimating the Potential for VitA Toxicity in Women and Young Children" J. Nutr., vol. 132, pp. 2907-2919 (2002).
Ames et al., "Biomedical studies on vitamin A. XIV. Biopotencies of Geometric Isomers of Vitamin A Acetate in the Rat", J. Am. Chem. Soc., vol. 77. pp. 4134-4136 (1955).
Asato et al., "Flourinated rhodopsin analogues from 10-flouro- and 14-flouroretinal", J. Am. Chem. Soc., vol. 100, No. 18, pp. 5957-5960 (1978).
Baehr et al., "The retinoid cycle and retina disease", Vision Research, vol. 43, pp. 2957-2958 (2003).
Bainbridge JW, et al. Effect of gene therapy on visual function in Leber's congenital amaurosis. The New England Journal of Medicine, www.nejm.org (Apr. 28, 2008); 358:2231-2239.
BASF, Technical information: Retinol 50C, 15D, and 10S. May 2005.
Batten ML et al., "Pharmacological and rAAV Gene Therapy Rescue of Visual Functions in a Blind Mouse Model of Leber Congenital Amaurosis," PL°S Medicine, 2(11)e:333; 1177-1189 (2005).
Batten, M.L. et al., "Lecithin-retinol Acyltransferase Is Essential for Accumulation of All-trans-Retinyl Esters in the Eye and in the Liver" J Biol Chem 279:10422-32 (2004 ).
Beischel, et al., "Azidotetraftuorophenyl Retinal Analogue: Synthesis and Bacteriorhodopsin Pigment Formation" Photochemistry and Photobiology, 60(1): 64-68 (1994).
Bernstein et al., "Biochemical characterization of the retinoid isomerase system of the eye", J. Biol. Chem., vol. 262, No. 35, pp. 16848-16857 (1987).
Berson et al., "Disease progression in patients with dominant retinitis pigmentosa and rhodopsin mutations", Invest. Opthalmol. Vis. Sci., vol. 43, No. 9, pp. 3027-3036 (2002).
Berson et al., "Further evaluation of docosahexaenoic acid in patients with retinitis pigmentosa receiving vitamin A treatment: subgroup analyses," Arch Ophthalmol., 122:1306-1314 (2004).
Berson et al., "Retinitis pigmentosa: unfolding its mystery" Proc. Natl. Sci. USA, vol. 93, pp. 4526-4528 (1996).
Berson, "Treatment of retinitis Pigmentosa with vitamin A", Digital J. Opthamol., vol. 4, No. 7 Massachusetts Eye and Ear Infirmary, Harvard Medical School (1998).
Berson, E.L., et al., "A Randomized Trial of Vitamin A and Vitamin E Supplementation for Retinitis Pigmentosa" Arch Ophthalmol 111, 761-772 (1993).
Biesalski et al., "Sensitive Analysis of Retinyl Esters by Isocratic Adsorption Chromatography", J. Clin. Chem. Clin. Biochem., vol. 27, No. 2, pp. 65-74 (1989) Abstract only.
Birch et al., "Validity and Reliability of the Children's Visual Function Questionnaire (CVFQ)" J AAPOS, 11(5); 473-479 (Oct. 2007).
Birnbach et al., "Retinoic acid accelerates photoreceptor cell death by apoptosis in Pro23HIS rhodopsin transgenic mice", Invest. Opthalmol. Vis. Sci., vol. 38, No. 4, pp. s311 (1997).
Bittner et al.,"test-retest, within-visit variability of goldmann visual fields in retinitis pigmentosa," Invest Ophthalmol Vis Sci, 52:8042-8046 (2011).
Boehm et al., "Photoaffinity Labeling Studies of Bacteriorhodopsin with [15-3H]-3-Diazo-4-keto-all-trans-retinal" J. Am. Chem. Soc., 112:1779-1782 (1990).
Borhan et al., "Chemoenzymatic Synthesis of 11-cis-Retinal Photoaffinity Analog by Use of Squid Retinochrome" J. Am. Chem. Soc., 119: 5758-5759 (1997).
Borhan, et al., "Efficient Synthesis of 11-cis-Retinoids" Chemistry (Europe) 5:1172-75 (1999).
Bridges, "Vitamin A* and the Role of the Pigment Epithelimn during Bleaching and Regeneration of Rhodopsin in the Frog Eye", Exp. Eye Res., vol. 22, pp. 435-455 (1976).
Buczylko et al., "Mechanisms of opsin activation", J. Biol. Chem., vol. 271, No. 34, pp. 20621-20630 (1996).
Caldwel et al., "Synthesis of Retinals with Eight- and Nine-Membered Rings in the Side Chain. Models for Rhodopsin Photobleaching Intermediates" J. Org. Chern., 58: 3533-3537 (1993).
Capecchi, "Altering the genome by homologous recombination", Science, vol. 244, No. 4910, pp. 1288-1292 (1989).
Carney and Russell, "Correlation of Dark Adaptation Test Results with Serum Vitamin A Levels in Diseased Adults", J. Nutr., vol. 110, pp. 552-557 (1980).
Caruso et al., "Effects of fenretinide (4-HPR) on dark adaptation", XP002475887; STN Database Accession No. 1998:418096 & Archives of Ophthalmology (Chicago), vol. 116, No. 6, pp. 759-763, Coden: Aropaw; ISSN:0003-9950, (1998) Abstract only.
Chan et al., "Delayed dark adaption caused by nilutamide", J. Neuro-Ophthalmology, vol. 28, No. 2, pp. 158-159 (2008).
Chapple et al., "Looking at protein misfolding neurodegenerative disease through retinitis pigmentosa", ACNR, vol. 3, Issue 1, pp. 12-13 (2003).
Chatzinoff et al., "Eleven-cis vitamin A in the treatment of retinitis Pigmentosa", Arch. Opthalmol., vol. 80, pp. 417-419 (1968).
Chen et al., "Inherent instability of the retinitis pigmentosa P23H mutant opsin", JBC Papers in Press, Manuscript M114.551713, 31 pages, Latest version can be accessed at http://www.jbc.org/cgi/doi/10.1074/jbc.M114.551713, Published Feb. 10, 2014.
Christoforidis, "Volume Of visual field assessed with kinetic perimetry and its application to static perimetry," Clin Ophthalmol, 5:535-541 (2011).
Cideciyan et al., "Human gene therapy for RPE65 isomerase deficiency activates the retinoid cycle of vision but with slow rod kinetics," PNAS USA., 105:15112-15117 (2008).
Cideciyan et al., "Rod and cone visual cycle consequences of a null mutation in the 11-cis-retinol dehydrogenase gene in man", Vis. Neurosci., vol. 17, No. 5, pp. 667-678 (2000).
Colenbrander "Visual Standards Aspects and Ranges of Vision Loss with Emphasis on Population Surveys" Report prepared for the International Council of Ophthalmology at the 29th International Congress of Ophthalmology Sydney, Australia, Apr. 2002, pp. 1-33.
Colmenares et al., "11, 12-Difluororhodopsin and Related Odd-Numbered Fluororhodopsins, The Use of JF,F for Following a Cis-trans Isomerization Process" J. Am. Chem. Soc., 121:5803-5804 (1999).

(56) References Cited

OTHER PUBLICATIONS

Congdon et al., "Responsiveness of dark-adaptation threshold to vitamin A and β-carotene supplementation in pregnant and lactating women in Nepal", Am. J. Clin. Nutr., vol. 72, pp. 1004-1009 (2000).
Corson et al., "Sensitization of bleach rod photoreceptors by 11-cis-locked analogues of retinal", PNAS USA, vol. 87, pp. 6823-6827 (1990).
Crescitelli et al., "Can Isorhodopsin be produced In the living rat?" Vision Res., 13(12):2515-2525 (1973).
Crescitelli et al., "The spectral properties and photosensitivities of analogue photopigments regenerated with 10- and 14-substituted retinal analogues" Proc. R. Soc. Lond. B 233: 55-76 (1988).
Crouch and Katz, "The effect of retinal isomers on the ver and erg of vitamin A deprived rats", Vision Res., vol. 20, pp. 109-115 (1980).
Crouch et al., "Cycloheptatrienylidene analog of 11-cis retinal", Invest. Opthalmol. Vis. Sci., vol. 25, pp. 419-418 (1984).
Crouch et al., "Inhibition of rhodopsin regeneration of cyclohexyl derivatives", Vision Research, vol. 22, No. 12, pp. 1451-1456 (1982).
Crouch et al., "Opsin pigments formed with acyclic retinal analogues Minimum 'ring portion' requirements for opsin pigment formation" FEBS 158:139-142 (1983).
Crouch et al., "Photosensitive pigments formed with rat opsin", Investigative Opthalmology, vol. 15, No. 10, pp. 872-875 (1976).
Crouch, "Yearly Review Studies of Rhodopsin and Bacteriorhodopsin Using Modified Retinals" Photochemistry and Photobiology, 44(6): 803-807 (1986).
Dahl et al., "Stability of vitamins in soybean oil fat emulsion under conditions simulating intravenous feeding of neonates and children" Journal of Parenteral Enteral Nutrition, 18:234-239 (1994).
De Grip et al., "10 20-methanorhodopsins (7E, 9E, 13E)-10 20 methanorhodopsin and (7E, 9Z, 13Z)-10 20-methanorhodopsin 11-cis-locked rhodopsin analog pigments with unusual thermal and photostability", Eur. J. Biochem., vol. 191, No. 1, pp. 211-220 (1990).
De Marchi et al. "Effects of isotretinoin on the metabolism of triglyceride-rich lipoproteins and on the lipid profile in patients with acne" Arch Dermatol Res, pp. 403-408, 2006.
DeLange et al., "An additional methyl group at the 10-position of retinal dramatically slows down the kinetics of the rhodopsin photocascade", Biochemistry, vol. 37, No. 5, pp. 1411-1420 (1998).
Den Hollander, A. I. et al., Prog Ret Eye Res 27:391-419, (2008).
Dorwald, Side Reactions in Organic Synthesis: A Guide to Successful Synthesis Design, Wiley-VCH Verlag GmbH & Co. KGaA, Weinheim, Preface p. IX, (2004).
Drachev et al., "An investigation of the electrochemical cycle of bacteriorhodopsin analogs with the modified ring", Arch. Biochem. Biophys., vol. 270, No. 1, pp. 184-197 (1989).
Driessen et al., "Disruption of the 11-cis-retinol dehydrogenase gene leads to accumulation of cis-retinols and cis-retinyl esters", Mol. Cell Biol., vol. 20, No. 12, pp. 4275-4287 (2000).
Ebrey et al., "Properties of Several Sterically Modified Retinal Analogs and Their Photosensitive Pigments", Biochemistry 14:3933-41 (1975).
European Search Report From related European Patent Application No. EP 04757476, search completed on Apr. 29, 2008.
European Search Report From Related European Patent Application No. EP 11154402, search completed on Sep. 5, 2011.
European Search Report From Related European Patent Application No. EP 11154404, search completed on Sep. 6, 2011.
European Search Report From Related European Patent Application No. EP 11154534, search completed on Sep. 5, 2011.
Eyring et al., "Assignment and Interpretation of Hydrogen Out-of-Plane Vibrations in the Resonance Raman Spectra of Rhodopsin and Bathorhodopsin" Biochemistry 21:384-93 (1982).
Fan et al., "Isorhodopsin rather than rhodopsin mediates rod function in rpe65 knock-out mice" PNAS, vol. 100, No. 23, pp. 13662-13667 (2003).
Fan J. et al. "Light Prevents Exogenous 11-cis Retinal from Maintaining Cone Photoreceptors in Chromophore-deficient Mice", Invest. Ophthalmoi.Vis Sci. Jan. 12, 2011, 10-6437.
Fazzi E, et al. Leber's congenital amaurosis: an update, Eur J Paediatr Neurol 2003; 7:13-22.
Fazzi E, et al. Response to pain in a group of healthy term newborns: behavior and physiological aspects. Functional Neurology 1996; 11:35-43.
Filipek S. et al., "G Protein-Coupled Receptor Rhodopsin: A Prospectus" Annu Rev Physiol 65:851-79 (2003).
Fujimoto et al., "On the Bioactive Conformation of the Rhodopsin" Chemistry 7:4198-204 (2001 ).
Fujimoto et al., "Solution and Biologically Relevant Conformations of Enantiomeric 11-cis-Locked Cyclopropyl Retinals" J. Am. Chem. Soc., 124: 7294-7302 (2002).
Fukada et al., "Studies on structure and function of rhodopsin by use of cyclopentatrienylidene 11-cis-locked rhodopsin", Biochemistry, vol. 23, No. 24, pp. 5826-5832 (1984).
Futterman et al., "The composition of liver vitamin A ester and the synthesis of vitamin A ester by liver microsomes", J. Biol. Chem., vol. 239, No. 12, pp. 4077-4080 (1964).
Gaffney et al., "Aging and cone dark adaptation", Optom. Vis. Sci., vol. 89, No. 8, pp. 1219-1224 (2012) (Abstract only).
Gao and Hollyfield, "Aging of the human retina" Inv. Opth. Vis. Sci., vol. 33, pp. 1-17 (1992).
Gartner et al., "Quantum Yield of Chapso-Solubilized Rhdopsin and 3-Hydroxy Retinal Containing Bovine Opsin" Photochemistry and Photobiology, 54(6): 1047-1055 (1991).
Gearhart PM, Gearhart C. Thompson DA, Petersen-Jones SM. "Improvement of visual performance with intravitreal administration of 9-cis-retinal in Rpe65-mutant dogs" Arch Ophthalmol 2010; 128(11):1442-8.
Gennaro et al., Remington: The Science and Practice of Pharmacy, 19th Edition, Mack Publishing Company, pp. 1528-1529 (1995).
Gerber, Le et al "Changes in Lipid Metabolism During Retinoid Administration" J. Amer. Acad. Derm., vol. 6, pp. 664-674 (1982).
Geroski et al., "Drug delivery for posterior segment eye disease", IOVS, vol. 41, No. 5, pp. 961-964 (2000).
Gollapalli, "All-trans-retinyl Esters are the Substrates for Isomerization in the Vertebrate Visual Cycle" D.R. et al., Biochemistry. 42(19):5809-5818 (2003).
Grant et al., "Treatable forms of retinitis pigmentosa associated with systemic neurological disorders", Int. Opthalmol. Clin., vol. 41, No. 1, (2001) printed from http://www.ncbi.nim.nih.gov/pubmed/11198137 on Jan. 14, 2009 Abstract only.
Grover et al., "Patterns of visual field progression in patients with retinitis pigmentosa," Ophthalmology, 105:1069-1075 (1998).
Gu S.M. et al., "Mutations in RPE65 Cause Autosomal Recessive Childhood-onset Severe Retinal Dystrophy," Nature Genetics, 17:194-7 (1997).
Haeseleer et al., "Dual-substrate specificity short chain retinol dehydrogenases from the vertebrate retina", J. Biol. Chem., vol. 277, No. 47, pp. 45537-45546 (2002).
Haig et al., "Vitamin A and Rod-Cone Dark Adaption in Cirrhoses of the Liver", Science, vol. 87, No. 2267, pp. 534-536 (1938).
Hamel CP, et al., "Molecular cloning and expression of RPE65, a novel retinal pigment epithelium-specific microsomal protein that is post-transcriptionally regulated in vitro," J Biol Chem, 268(21):15751-15757 (1993).
Han et al., "The C9 methyl group of retinal interacts with glycine-121 in rhodopsin" Proc. Natl. Acad. Sci. USA, 94: 13442-13447 (Dec. 1997).
Handbook of Pharmaceutical Excipients, Fifth Ed., Soybean Oil, pp. 722-723 (3 pgs total) (2006).
Hartong et al., "Retinitis pigmentosa," Lancet, 368:1795-1809 (2006).
Harvard Health Publications, "The aging eye: preventing and treating eye disease", Harvard Health Publications, 3 pgs. (2011) printed from http://www.health.harvard.edu/special_health_reports/the_Aging_Eye on Nov. 5, 2011.
Head, "Natural therapies for ocular disorders, part one: diseases of the retina", Alt. Med. Review, vol. 4, No. 5, pp. 342-359 (1999).

(56) References Cited

OTHER PUBLICATIONS

Hiraki et al., "Bacteriorhodopsin Analog Regenerated with 13-Desmethyl-13-Iodoretinal" Biophys. J. 83:3460-69 (2002).
Hirano et al., "Constraints of Opsin Structure on the Ligand-binding Site: Studies with Ring-fused Retinals" Photochemistry and Photobiology, 76(6): 606-615 (2002).
Hisatomi et al., "Critical role of photoreceptor apoptosis in functional damage after retinal detachment", Curr. Eye Res., vol. 24, No. 3, 161-172 (2002) Abstract only, 1 pg., printed from http://www.ncbi,nim.nih.gov/pubmed/12221523.
Howard et al., "Comparative distribution, pharmacokinetics and placental permeabilities of all-trans-retinoic acid, 13-cis-retinoic acid, all-trans-4-oxo-retinoic acid, retinyl acetate and 9-cis-retinal in hamsters", Arch. Toxicol., vol. 63, pp. 112-120 (1989).
Hu et al., "Unbleachable Rhodopsin with an 1 1 ~cis~Locked Eight~Membered Ring Retinal: The Visual Transduction Process" Biochemistry, 33:408-416 (1994).
Imanishi et al., "Noninvasive two-photon imagine reveals retinyl ester storage structures in the eye" The Journal of Cell Biology, 164(3):373-383 (2004).
International Search Report from related PCT Patent Application No. PCT/US2004/007937 dated Dec. 3, 2004, application now published as International Publication No. WO2004/082622, published on Sep. 30, 2004.
International Search Report dated Oct. 27, 2011 for PCT/US2009/059126.
Jackson et al., "aging and scotopic sensitivity", Vis. Res., vol. 38, pp. 3655-3662 (1998).
Jackson et al., "Photoreceptor degeneration and dysfunction in aging and age-related maculopathy", Aging Res. Rev., vol. 1, No. 3, pp. 381-396 (2002).
Jackson, G.R. et al,. "Aging and Dark Adaptation" J. Vision Research 39: 3975-3982 (1999).
Jacobson et al., "Defining the Residual Vision in Leber Congenital Amaurosis Caused by RPE65 Mutations" Investigative Ophthalmology & Visual Science, 50(5): 2368-2375 (May 2009).
Jacobson et al., "Identifying photoreceptors in blind eyes caused by RPE65 mutations: Prerequisite for human gene therapy success", PNAS USA, vol. 102, No. 17, pp. 6177-6182 (2005).
Jacobson et al., "Phenotypic Marker for Early Disease Detection in Dominant Late-Onset Retinal Degeneration", IOVS, vol. 42, No. 8, pp. 1882-1890 (2001).
Jacobson et al., "Retinal degenerations with truncation mutations in the cone-rod homeobox (CRX) gene", Invest. Opthalmol. Vis. Sci., vol. 39, No. 12, pp. 2417-2426 (1988).
Jacobson, S.G., et al., "Night Blindness in Sorsbys Fundus Dystrophy Reversed by Vitamin A" Nat Genet 11, 27-32 (1995).
Jang et al., "Characterization of a dehydrogenase activity responsible for oxidation of 11-cis-retinol in the retinal pigment epithelium of mice with a disrupted RDH5 gene. A model for the human heredity disease fundus albunctatus", J. Biol. Chem., vol. 276, No. 35, pp. 32456-32465 (2001).
Jang et al., "Mechanism of Rhodopsin Activation as Examined with Ring-constrained Retinal Analogs and the Crystal Structure of the Ground State Protein" The Journal of Biological Chemistry, 276(28): 26148-26153, (Jul. 13, 2001 ).
Jin et al., "Noncovalent occupancy of the retinal-binding pocket of opsin diminishes bleaching adaption of retinal cones", Neuron, No. 11, pp. 513-522 (1993).
Jin M, et al. Rpe65 is the retinoid isomerase in bovine retinal pigment epithelium. Cell 2005; 122:449-459.
Karnaukhova et al., "Bioactivity of Visual Pigments with Sterically Modified Retinal Analogs" Bioorganic Chemistry 27:372-82 (1999).
Kefalov et al., "Role of noncovalent binding of 11-cis-retinal to opsin in dark adaption of rod and cone photoreceptors", Neuron, vol. 29, pp. 749-755 (2001).
Kemp et al., "Visual Function and Rhodopsin Levels in Humans with Vitamin A Deficiency", Exp. Eye Res., vol. 46, pp, 185-197 (1988).

Kirillova et al., "Cyclopentene and cyclohexene retinal analogues react differently with bacteriorhodopsin", Chemical Abstracts, vol. 120, pp. 557, (1994) Abstract No. 120:187138 Abstract only.
Klein et al., "Psychophysical assessment of low visual function in patients with retinal degenerative diseases (RODS) with the Diagnosys full-field stimulus threshold (D-FST)" Doc Ophthalmol, 119:217-224 (2009).
Koenekoop et al., "Oral 9-cis retinoid for childhood blindness due to Leber congenital amaurosis caused by RPE65 or LRAT mutations: an open-label phase 1b trial", Lancet, 8 pages, Published Online http://dx.doi.org/10.1016/S0140-6736(14)60153-7, Published Jul. 14, 2014.
Koenekoop, R.K. et al.: Oral Synthetic cis-Retinoid Therapy in Subjects with Leber Congenital Amauarosis (LCA) due to Lecithin-Retinal Acyltransferase (LRAT) or Retinal Pigment Epithelial 65 Protein (RPE65) Mutations: Preliminary Results of a Phase 1b Open-Label Trial, Poster presented at Annual Meeting of the Association for Researach in Vision and Opthamology (ARVO), May 2011. http://www.qltinc.com/development/products/documents/QLT091001-LCA-ARVO_2011_poster.pdf.
Koenekoop, RK., "Oral synthetic cis-retinoid therapy in subjects with Leber Congenital Amaurosis (LCA) due to Lecithin:Retinol Acyltransferase (LRAT) or Retinal Pigment Epithelial 65 Protein (RPE65) mutations: Preliminary Results of a Phase 1b Open Label Trial" Invest: Ophthalmol. Vis. Sci. 2011; 52: E-Abstract 3323.
Koutalos "Regeneration of Bovine and Octopus Opsins in Situ with Natural and Artificial Retinals" Biochemistry 28:2732-39 (1989).
Kozlov et al., "Oxidation of Vitamin A Acetate in Soybean Oil," Khimiko-Farmatsevti-cheskii Zhurnal, 10:24-29 (1971) (English translation).
Kubo et al., "Effect of vitamin A palmitate on vitamin A~deficient rabbits", XP002475885; STN Database Accession No. 2000:172779 & Nippon Ganka Gakkai Zasshi, vol. 103, No. 10, pp. 729-733 Coden:NGZAA6; ISSN: 0029-0203,1999 Abstract only.
Kuksa et al., "Biochemical and Physiological Properties of Rhodopsin Regenerated with 11-cis-6-Ring- and 7-Ring-retinals" The Journal of Biological Chemistry, 277(44): 42315-42324 (Nov. 1, 2002).
Kuksa et al., Retinoid cycle in the vertebrate retina: experimental approaches and mechanisms of isomerization, Vision Research, vol. 43, pp. 2959-2981 (2003).
Kupfer et al., "Information for doctors who follow patients with retinitis pigmentosa", National Eye Institute (1993), printed from http://www.nei.nih.gov/news/clinicalalerts/alert-rp.asp on Jan. 15, 2009, 2 pages.
Kuse et al., "Change in retinal rod function in age-related macular degeneration," Japanese Review of Clinical Ophthalmology, vol. 10, No. 100, pp. 59 (English Abstract only) (2006).
Lamb and Pugh, "Phototransduction, Dark Adaptation, and Rhodopsin Regeneration", IOVS, vol. 47, No. 12, pp. 5138-5152 (2006).
Lamb, T.D. et al,. "Dark Adaptation and the Retinoid Cycle of Vision" J. Prog Retin Eye Res 23, 307-380 (2004).
Lang, "Ocular drug delivery conventional ocular formulations", Adv. Drug Del. Rev., vol. 16, No. 1, pp. 39-43 (1995).
Lawson et al., "Retinal analog restoration of photophobic responses in a blind chlamydomonas-reinhardtii mutant evidence for an archaebacterial like chromophore in a eukaryotic rhodopsin", Biophysical Journal, vol. 60, No. 6, pp. 1490-1498 (1991).
Lewin et al., "Synthesis and Characterization of trans-, 13-cis-, and 11-cis , 13-cis-12-(Hydroxymethyl)retinols" J. Org. Chem., 49: 649-652 (1984).
Lewis et al., "Steric Barrier to Bathorhodopsin Decay in 5-Demethyl and Mesityl Analogues of Rhodopsin" J. Am. Chem. Soc., 123: 10024-10029 (2001).
Li et al., "Delivery of 9-cis retinal to photoreceptors from bovine serum albumin", Photochem. Photobiol., vol. 69, No. 4, pp. 500-504 (1999).
Li et al., "Effect of vitamin A supplementation on rhodopsin mutants threonine-17→methionine and proline~347→serine in transgenic mice and in cell cultures", Proc. Natl. Acad. Sci. USA, vol. 95, pp. 11933-11938 (1998).

(56) References Cited

OTHER PUBLICATIONS

Lin et al., "Vibrational Assignment of Torsional Normal Modes of Rhodopsin Probing Excited-State Isomerization Dynamics along the Reactive C11dC12 Torsion Coordinate" J. Phys. Chem. B, 102:2787-2806 (1998).
Littink et al., "A homozygous frameshift mutation in LRAT causes retinitis punctata albescens," Ophthalmology, 119:1899-1906 (2012).
Liu et al., "The nature of restrictions in the binding site of rhodopsin. A model study", J. Am. Chem. Soc., vol. 106, No. 26, pp. 8298-8300 (1984).
Lorenz B, et al. Early-onset severe rod-cone dystrophy in young children with RPE65 mutations. Investigative Ophthalmology & Visual Science 2000; 41:2735-2742.
Lorenz et al., "A comprehensive clinical and biochemical functional study of a novel RPE65 hypomorphic mutation," Invest Ophthalmol Vis Sci, 49:5235-5242 (2008).
Maeda A, et al., "Role of photoreceptor-specific retinol dehydrogenase in the retinoid cycle in vivo," J Biol Chem, 280(19):18822-18832 (2005).
Maeda et al., "Effects of Long-Term Administration of 9-cis-Retinyl Acetate on Visual Function in Mice", Investigative Ophthalmology & Visual Science, Jan. 2009, vol. 50, No. 1, pp. 322-333.
Maeda et al., "Evaluation of the role of the retinal g protein-coupled receptor (RGR) in the vertebrate retina in vivo", Journal of Neurochemistry, vol. 85, pp. 944-956 (2003).
Maeda et al., "Improvement in Rod and Cone Function in Mouse Model of *Fundus albipunctatus* after Pharmacologic Treatment with 9-cis-Retinal", IOVS, vol. 47, No. 10, pp. 4540-4546 (2006).
Maeda et al., "QLT91001, a 9-cis-Retinal Analog, Is Well-Tolerated by Retinas of Mice with Impaired Visual Cycles," Investigative Ophthalmology & Visual Science, 54(1):455-466, (2013).
Maeda T, et al., "A Critical Role of CaBP4 in the Cone Synapse," Investigative Ophthalmology & Visual Science, 46(11):4320-4327 (2005).
Maeda T, et al., "Loss of cone photoreceptors caused by chromophore depletion is partially prevented by the artificial chromophore prodrug, 9-cis-retinyl acetate," Human Molecular Genetics 18(12): 2277-2287 (2009). Published on-line Apr. 1, 2009.
Maeda, T. et al., "Evaluation of 9-cis-Retinyl Acetate Therapy in Rpe65−/− Mice," Investigative Ophthalmology & Visual Science, (50)9:4368-4378 (2009).
Maguire et al., "Safety and Efficacy of Gene Transfer for Leber Congenital Amaurosis" Supplementary Appendix from N Engl J Med, 358: 2240-8 (2008).
Maguire et al., "Safety and Efficacy of Gene Transfer for Leber's Congenital Amaurosis" N Engl J Med, 358: 2240-8 (2008).
Margaron, P., Castaner, L., and Narfstrom, K. "Evaluation of Intravitreal cis-Retinoid Replacement Therapy in a Canine Model of Leber's Congenital Amaurosis" Invest Ophthalmol Vis Sci; 50:E-Abstract 6280 (2009).
Marlhens F, et al. Mutations in Rpe65 cause Leber's congenital amaurosis. Nature Genetics 1997; 17:139-141.
Marlhens, F. et al., "Autosomal recessive retinal dystrophy associated with two novel mutations in the RPE65 gene" Eur J Hum Genet. 6(5):527-531 (1998).
Marmor et al., "Abipunctate retinopathy with cone dysfunction and no abnormality in the RDH5 or RLBP1 genes", Retina, vol. 23, No. 4, pp. 543-546 (2003).
Massoud et al., "Plasma vitamin A and beta-carotene in retinitis pigmentosa", Brit. J. Opthal., vol. 59, pp. 200-204 (1975).
Mata et al.,"Substrate specificity of retinyl ester hydrolase activity in retinal pigment epithelium", Journal of Lipid Research, vol. 39, pp. 604-612 (1998).
Matsukawa et al., "Role of purpurin as a retinal-binding protein in goldfish retina during the early stage of optic nerve regeneration: Its priming action on neurite outgrowth", J. Neurosci., vol. 24, No. 38, pp. 8346-8353 (2004).
Maugard et al., "Enzymatic synthesis of derivatives of vitamin A in organic media", J. Mol. Cat. B, vol. 8, pp. 275-280 (2000).
Maugard et al., "Synthesis of water-soluble retinol derivatives by enzymatic method", Botechnol. Prog. vol. 18, pp. 424-428 (2002).
Maxwell et al., "Photodynamic Response in Rhodotorula Glutinis in The Abscence of Added Sensitizers" Photochemistry and Photobiology, val. 13, pp. 259-273 (1971).
Mayo Clinic, "Retinal detachment", 8 pgs. (2010) printed from http://www.mayoclinic.com/health/retinal-detachment/DS00254/METHOD=print&DSECTION=all.
McBee et al., "Isomerization of 11-cis-retinoids to all-trans-retinoids in vitro and in vivo", J. Biol. Chem., vol. 276, No. 51, pp. 48483-48493 (2001).
McBee, J.K. et al., "Confronting Complexity: the Interlink of Phototransduction and Retinoid Metabolism in the Vertebrate Retina" Prog Retin Eye Res 20, 469-529 (2001).
MedlinePlus, "Diabetic retinopathy", 5 pgs. (2011) printed from http://www.nim.nih.gov/medlineplus/ency/article/00212.htm.
Mendes et al., "Pharmacological manipulation of rhodopsin retinitis pigmentosa", Advances in Experimental Medicine and Biology, Chapter 36, pp. 317-323, DOI 10.1007/978-1-4419-1399-9_36, Springer Science+Business Media, LLC (2010).
Mizukami et al., "Photoisomerization mechanism of the rhodopsin chromophore: Picosecond photolysis of pigment containing 11-cis-locked eight-membered ring retinal" Proc. Natl. Acad. Sci. USA, 90:4072-4076 (May 1993).
Moise et al.. "Delivery of Retinoid-Based Therapies to Target Tissues" Biochemistry. 46(15): 4449-4458 (2007).
Moiseyev G. et al., "RPE65 is the isomerohydrolase in the retinoid visual cycle," Proceedings of the National Academy of Sciences of the United States of America,102(35):12413-12418 (2005).
Morimura, H. et al., "Mutations in the RPE65 gene in patients with autosomal recessive retinitis pigmentosa or Leber congenital amaurosis" Proc Natl Acad Sci USA. 95(6):3088-3093 (1998).
Myhre et al., "Water-miscible, emulsified, and solid forms of retinol supplements are more toxic than oil-based preparations[1-3]," Am. J. Clin. Nutr., 78(6):1152-9 (2003).
Nakamura et al., "A high association with cone dystrophy in fundus albipunctatus caused by mutations of the RDH5 gene", Invest. Opthalmol. Vis. Sci., vol. 41. No. 12, pp. 3925-3932 (2000).
Newton et al., "Structure-Activity Relationships of Retinoids in Hamster Tracheal Organ Culture", Cancer Res., vol. 40, pp. 3413-3425 (1980).
Nishiguchi et al., "A novel mutation (I143NT) in guanylate cyclase-activating protein 1 (GCAP1) associated with autosomal dominant cone degeneration", Invest. Opthalmol. Vis. Sci., vol. 45, No. 11, pp. 3863-3870 (2004).
Noell, "Suitability of retinol, retinal and retinyl palmitate for the regeneration of bleached rhodopsin in the isolated frog retina", XP002486105, STN Database Accession No. 1985:164043 & Vision Research, vol. 24, No. 11, pp. 1615-1622, CODEN:VISRAM; ISSN:0042-6989, (1984) Abstract only.
Noorwez et al., "Pharmacological chaperone-mediated in vivo folding and stabilization of the P23H-opsin mutant associated with autosomal dominant retinitis Pigmentosa", J. Biol. Chem., vol. 278, No. 16, pp. 14442-14450 (2003).
Noorwez et al., "Retinoids assist the cellular folding of the autosomal dominant retinitis Pigmentosa opsin mutant P23H", J. Biol. Chem., vol. 279, No. 16, pp. 16278-16284 (2004).
Norum and Blomhoff, "McCollum Award Lecture, 1992: Vitamin A absorption, transport, cellular uptake, and storage", Am. J. Clin. Nutr., vol. 56, pp. 735-744 (1992).
O'Byrne et al., "Retinoid Absorption and Storage Is Impaired in Mice Lacking Lecithin:Retinol Acyltransferase (LRAT)" The Journal of Biological Chemistry, 280(42): 35647-35657 (Oct. 21, 2005).
Ohgane et al., "Retinobenzaldehydes as proper-trafficking inducers of folding-defective p23H rhodopsin mutant responsible for retinitis pigmentosa", Bioorg. Med. Chem., vol. 18, pp. 7022-7028 (2010).
Owsley et al., "Delays in rod-mediated dark adaption in early age-related maculopathy", Ophthalmology, vol. 108, No. 7, pp. 1196-1202 (2001).
Owsley et al., "Development of a Questionnaire to Assess Vision Problems under Low Luminance in Age-Related Maculopathy" Investigative Ophthalmology & Visual Science, 47(2): 528-535 (Feb. 2006).

(56) References Cited

OTHER PUBLICATIONS

Owsley et al., "Effect of short-term, high-dose retinol on dark adaption in aging and early age-related maculopathy", Invest. Ophthalmol. Vis. Sci., vol. 47, No. 4, pp. 1310-1318 (2006).
Paik et al., "9-cis-retinoids: biosynthesis of 9-cis-retinoic acid", Biochemistry, vol. 39, No. 27, pp. 8073-8084 (Jul. 2000).
Palczewski K. G protein-coupled receptor rhodopsin. Annual Review of Biochemistry 2006; 75:743-767.
Pang JJ, et al. Retinal degeneration 12 (rd12): a new, spontaneously arising mouse model for human Leber congenital amaurosis (LCA). Molecular Vision 2005; 11:152-162.
Park et al., "Toward a clinical protocol for assessing rod, cone, and melanopsin contributions to the human pupil response," Invest Ophthalmol Vis Sci, 52(9):6624-6635 (2011).
Parry et al., "Visual pigment reconstitution in intact goldfish retina using synthetic retinaldehyde isomers", Vision research, vol. 40, No. 17, pp. 2241-2247 (2000).
Pearlman et al., "Visual Pigments of the Vitamin A-Deficient, Thyroidectomized Rat Following Vitamin $A_2$ Administration," Vision Res., 11(3):177-187 (1971).
Perrault I, et al. Leber congenital amaurosis. Mol Genet Metab 1999; 68:200-208.
Perusek et al., "Vitamin A Derivatives as Treatment Options for Retinal Degenerative Diseases," Nutrients, 5:2646-2666 (2013).
Phelan, J.K. et al., "A Brief Review of Retinitis Pigmentosa and the Identified Retinitis Pigmentosa Genes" Mol Vis. 6:116-124 (2000).
Price et al., "Mislocalization and degradation of human P23H-Rhodopsin-GFP in a knockin mouse model of retinitis pigmentosa", Inv. Opth. Vis. Sci., vol. 52, No. 13, pp. 9728-9736 (2011).
QLT INC. Press release: "QLT Announces Results from Phase 1b Trial of QLT091991 in Subjects with Leber Congenital Amaurosis," May 3, 2011 (May 2, 2011), http://www.qltinc.com/newsCenter/2011/110503.htm. See entire document.
Radomska et al., "The use of some ingredients for microemulsion preparation containing retinol and its esters", XP002475886, STN Database Accession No. 2000:139945 & International Journal of Pharmaceutics, vol. 196, No. 2, pp. 131-134 Coden:IJHDEI; ISSN; 0378-5173, (2000) Abstract only.
Rao et al., "5-(Triftuoromethyl)bacteriorhodopsin Does Not Translocate Protons" J. Am. Chem. Soc. 108:6077-78 (1986).
Rao et al., "Isomers of 3, 7, 11-trimethylododeca-2, 4, 6, 8, 10-pentaenal (A linear analogue of retinal) and lower homologues in their interaction with bovine opsin and bacterioopsin", Photochemistry and Photobology, vol. 41, No. 2, pp. 171-174 (1985).
Rao et al., "Regioselective photo isomerisation of retinolacetate" Tetrahedron Letters, vol. 31, No. 24, pp. 3441-3444 (1990).
Redmond TM, et al., "Mutation of key residues of RPE65 abolishes its enzymatic role as isomerohydrolase in the visual cycle," Proceedings of the National Academy of Sciences of the United States of America, 102(38):13658-13663 (2005).
Redmond, T.M. et al., "Rpe65 is necessary for production of 11-cis-vitamin A in the retinal visual cycle" Nature Genetics, 20:344-351 (1998).
Reid et al., "Mass Spectral Analysis of Eleven Analogs of Vitamin A1" Lipids, 8(10): 558-565.
Renk, et al., "A Rhodopsin Pigment Containing a Spin-Labeled Retinal" J. Am. Chem. Soc. 109:6163-6168 (1987).
Revised, Pharmaceutical Additive Handbook (Kaitei Iyakuhin Handobukku), Yakuji Nippo Limited, Feb. 28, 2007, p. 753-755.
Rezabek et al., "Effects of dietary retinyl acetate on the promotion of hepatic enzyme-altered foci by polybrominated biphenyls in initiated rats", Food Chem. Toxicol., vol. 27, No. 8, pp. 539-544 (1989) Abstract only.
Ridge KD et al. Visual rhodopsin sees the light: structure and mechanism of G protein signaling. J Biol Chem 2007; 282(13):9297-9301.
Robinson et al., "Opsins with mutations at the site of chromophore attachment constitutively activate transducin but are not phosphorylated by rhodopsin kinase", Proc. Natl. Acad. Sci. USA, vol. 91, No. 12, pp. 5411-5415 (1994).

Roman et al., "Full-field stimulus testing (EST) to quantify visual perception in severely blind candidates for treatment trials" Physiol. Meas. 28: N51-N56 (2007).
Rotenstreich et al., "Treatment of a retinal dystrophy, fundus albipunctatus, with oral 9-cis-b-carotene", Br. J. Opthalmol., vol. 94, pp. 616-621 (2010).
Rotenstreich et al., "Treatment with 9-cis β-carotene-rich powder in patients with retinitis pigmentosa; a randomized crossover trial," JAMA Ophthalmol., 131:985-992 (2013).
Russell, "The vitamin A spectrum: from deficiency to toxicity", Am. J. Clin. Nutr., vol. 71, pp. 878-884 (2000).
Sakami et al., "Probing mechanisms of photoreceptor degeneration in a new mouse model of the common form of autosomal dominant retinitis pigmentosa due to P23H opsin mutations", JBC Papers in Press, Manuscript M110.209759, 29 pages, Latest version can be accessed at http://www.jbc.org/cgi/doi/10.1074/jbc.M110.209759, Published Jan. 11, 2011.
Saliba et al., "The cellular fate of mutant rhodopsin: quality control, degradation and aggresome formation", J. Cell Science, vol. 115, pp. 2907-2918 (2002).
Sandberg et al., "Clinical expression correlates with location of rhodopsin mutation in dominant retinitis Pigmentosa", Invest. Opthalmol. Vis. Sci., vol. 36, No. 9, pp. 1934-1942 (1995).
Schatz et al., "Fundus albipunctatus associated with compound heterozygous mutations in RPE65," Ophthalmology, 118:888-894 (2011).
Sekiya, et al., "Effect of modification of the chromophore in retinochrome" Biophys. Chem. 56:31-39 (1995).
Semenova et al., "Stabilization of all-trans-retinol by cyclodextrins: a comparative study using hplc and fluorescence spectroscopy", XP002475883; STN Database Accession No. 2003:494986 & Journal Of Inclusion Phenomena and Macrocyclic Chemistry, Volume Date (2002), vol. 44, No. 1-4, pp. 155-158 Coden:JIPCF5; ISSN:1388-3127, (2003) Abstract only.
Semenova et al., "Systems for delivery of vitamin A to the retina in retinitis pigmentosa", XP002475884; STN Database Accession No. 2002:438129 & New Insights Into Retinal Degenerative Diseases, [Proceedings Of The International Symposium On Retinal Degeneration], 9TH, Durango, Co, United States, (2000), Meeting Date (2000), pp. 105-110; Editor (Anderson & Lavail), (2001) Abstract only.
Semple-rowland et al., "A null mutation in the photoreceptor guanylate cyclase gene causes the retinal degeneration chicken phenotype", Proc. Natl. Acad. Sci. USA, vol. 95, No. 3, pp. 127-1276 (1998).
Sen et al.. "Synthesis and Binding Studies of a Photoaffinity Label for Bovine Rhodopsin" J. American Chem. Soc. 104:3214-16 (1982).
Sibulesky et al., "Safety of <7500 RE (<25000 IU) vitamin A daily in adults with retinitis Pigmentosa", Am. J. Clin. Nutr., vol. 69, pp. 656-663 (1999).
Silverman, AK "Hypervitaminosis A Syndrome: A Paradigm of Retinoid Side Effects", J. Am. Acad. Derm., vol. 16, pp. 1027-1039 (1987).
Sokal et al., "GCAP1 (Y99C) mutant is constitutively active in autosomal dominant cone dystrophy", Mol. Cell. vol. 2, No. 1, pp. 129-133 (1998).
Soriatane® (acitretin) capsule US Label (2009) and Principal Display Panels (24 pages).
Spaeth, Ophthalmic Surgery: Principles of Practice, Ed., W. B. Sanders Co., Philadelphia, Pa., U.S.A., pp. 85-87 (1990).
Stecher et al., "Preferential release of 11-cis-retinol from retinal pigment epithelial cells in the presence of cellular retinaldehyde-binding protein" The Journal of Biological Chemistry, vol. 274, No. 13, pp. 8577-8585 (1999).
Steinberg et al., "Isomer Composition and Spectra of the Dark and Light Adapted Forms of Artificial Bacteriorhodopsins" Photochemistry and Photobiology, 54(6) 969-976 (1991).
Supplementary European Search Report From Related European Patent Application No. EP 05773576, dated Aug. 4, 2008.

(56) References Cited

OTHER PUBLICATIONS

Taha E I. et al. Preparation and in vitro characterization of self-nanoemulsified drug delivery system (SNEDDS) of all-trans-retinol acetate. International Journal of Pharmaceutics. 2004; 285(1-2): 109-119.
Tan et al., "Absolute Sense of Twist of the C12-C13 Bond of the Retinal Chromophore in Bovine Rhodopsin Based on Exciton-Coupled CD Spectra of 11, 12-Dihydroretinal Analogues" Anxeu Cben7 Inr Ed Engl 36(19): 2089-2093 (1997).
Targretin® (bexarotene) capsule US Label (2006) (14 pages).
Tarkhov et al., "Study of a structure-property relationship for retinal derivatives taking into account their conformational flexibility", Chemical Abstracts, vol. 128, No. 18, pp. 270 (1998) Abstract No. 128:214600 Abstract only.
Teelmann, K "Retinoids: Toxicity and Teratogenicity to Date," Pharmac. Ther., vol. 40, pp. 29-43 (1989).
Teller et al., "Advances in determination of a high-resolution three-dimensional structure of rhodopsin, a model of G-protein-coupled receptors (GPCRs)", Biochemistry vol. 40, No. 26, pp. 7761-7772 (2001).
The Eye Digest, "Aging eye in the US", 2 pgs. (2011) printed from http://web.archive.org/web/20060810014820/http://www.agingeye.net/mainnews/usaging.php.
The K-Zone, Biophysical data tables: standard man, Jul. 2004 printed Mar. 14, 2009 from http:/www.kevinboone.com/biodat_stdman.html, 1 page.
Thompson DA, et al., "Genetics and phenotypes of RPE65 mutations in inherited retinal degeneration," Investigative Ophthalmology & Visual Science, 41(13):4293-4299 (2000).
Thompson et al., "Genetic defects in vitamin A metabolism of the retinal pigment epithelium", Genetics in Ophthalmology, vol. 37, pp. 141-154 (2003).
Thompson, D.A. et al., "Mutations in the Gene Encoding Lecithin Retinol Acyltransferase Are Associated With Early-Onset Severe Retinal Dystrophy" Nat Gen 28:123-4 (2001).
Thomson Scientific, London, GB; AN 1995-063773, XP002475888 & JP 06340525 A (Lion Corp); Dec. 13, 1994 Abstract only.
Thomson Scientific, London, GB; AN 1996-408307, XP002475889 & JP 08198746 A (Lion Corp); Aug. 6, 1996 Abstract only.
Thomson Scientific, London, GB; An 1998-518867, XP002475890 & RU 2106843 C1 (Krasy Med Acad); Mar. 20, 1998 Abstract only.
Toctinon™ (alitretinoin) capsule Canadian Product Monograph (2011) (34 pages).
Travis, G.H. et al., "Diseases Caused by Defects in the Visual Cycle: Retinoids as Potential Therapeutic Agents" Annu Rev Pharmacol Toxicol, 47:469-512 (2007).
Tsujikawa M. et al., "Age at Onset Curves of Retinitis Pigmentosa" Arch Ophthalmol 126(3) 337-340 (2008).
V.G. Byelikov, Farmatsevticheskaya khimiya, [Pharmaceutical Chemistry], M., Vysshaya shkola, 1993, pp. 43-47 (Russian language and the English translation).
Van Hooser et al., "Rapid restoration of visual pigment and function with oral retinoid in a mouse model of childhood blindness" PNAS, 97(15): 8623~8628 (Jul. 18, 2000).
Van Hooser et al., "Recovery of Visual Functions in a Mouse Model of Leber Congenital Amaurosis" The Journal of Biological Chemistry, 277(21):19173-19182 (2002).
Vesanoid® (tretinoin) capsule US Label (2004) (14 pages).
Vitamin Converter, known vitamin A conversion, 3 pgs., printed from http;//www.robert-forbes.com/resources/vitaminconverter.html on Apr. 19, 2012.
Von Lintig, J. et al., "The biochemical and structural basis for trans-to-cis isomerizatian of retinoids in the chemistry of vision" Trends Biochem Sci Feb. 24, 2010.
Wada et al., "Retinoids and related compounds. Part 20.1 Synthesis of (11Z)-8, 18-ethanoretinal and a conformational study of the rhodopsin chromophore" J. Chem. Soc., Perkin Trans. 1: 1773-1777 (1997).
Wada et al., "Retinoids and related compounds. Part 26.1 Synthesis of (11Z)-8, 18-propano- and methano-retinals and conformational study of the rhodopsin chromophore" J. Chem. Soc., Perkin Trans. 1:2430-2439 (2001).
Weiser and Somorjai, "Bioactivity of cis and dicis isomers of vitamin A esters", Internatl. J. Vit. Nutr., vol. 62, pp. 201-208 (1992).
Wingerath et al.. "Analysis of Cyclic and Acyclic Analogs of Retinol. Retinoic Acid, and Retinal by Laser Desorption Ionization~, Matrix-Assisted Laser Desorption ionization±Mass Spectrometry, and UV/Vis Spectroscopy" Analytical Biochemistry 272:232-242 (1999).
Witkovsky et al., "Formation, conversion, and utilization of isorhodopsin, rhodopsin, and porphyropsin by rod photoreceptors in the xenopus retina", J. Gen. Physiol., vol. 72, pp. 821-836 (1978).
Woodward et al., "The inflow and outflow of anti-glaucoma drugs", Trends Pharm. Sci., vol. 25, No. 5, pp. 238-241 (2004).
Wrigstad A, et al. Ultrastructural changes of the retina and the retinal pigment epithelium in Briard dogs with hereditary congenital night blindness and partial day blindness. Experimental Eye Research 1992: 55:805-818.
www.wrongdiagnosis.com, "Symptom: night blindness", pp. 1-17 (Jun. 3, 2008).
Yamamoto et al., "Mutations in the gene encoding 11-cis retinol dehydrogenase cause delayed dark adaptation and fundus Albipunctatus", Nat. Genet., vol. 22, No. 2, pp. 188-191 (1999).
Yamamoto et al.,"Important role of the proline residue in the signal sequence that directs the secretion of human lysozyme in Saccharomyces cerevisiae", Biochemistry, vol. 28, pp. 2728-2732 (1989).
Yan et al., "Mechanism of activation of sensory rhodopsin 1: Evidence for a steric trigger" Proc. Natd. Acad. Sci. USA, 88:9412-9416 (Nov. 1991).
Yanai D, et al., "Visual performance using a retinal prosthesis in three subjects with retinitis pigmentosa," American Journal of Ophthalmology, 143(5):820-827 (2007).
Yoshikami et al., "Visual Pigments of the Vitamin A-Deficient Rat Following Vitamin $A_2$ Administration," Vision Res., 9(6):633-646 (1969).
Yoshizawa et al., "Photochemistry of Iodopsin" Nature, 214: 566-571 (May 6, 1967).
Zankel et al., "Bovine rhodopsin with 11-cis-locked retinal chromophore neither activates rhodopsin kinase nor undergoes conformational change upon irradiation", J. American Chemical Soc., vol. 112, No. 13, pp. 5387-5388 (1990).
Zech LA et al. "Changes in Plasma Cholesterol and Triglyceride Levels After Treatment with Orallsotretinoin" Arch. Dermatol., vol. 119, pp. 987-993 (1983).
Zhang et al.. "Structure, alternative splicing, and expression of the human RGS9 gene", Gene, vol. 240, pp. 23-24 (1999).
Zhu et al., "A naturally occurring mutation of the opsin gene (T4R) in dogs affects glycosylation and stability of the G protein-coupled receptor", J. Biol. Chem., vol. 279, No. 51, pp. 53828-53839 (2004).

* cited by examiner

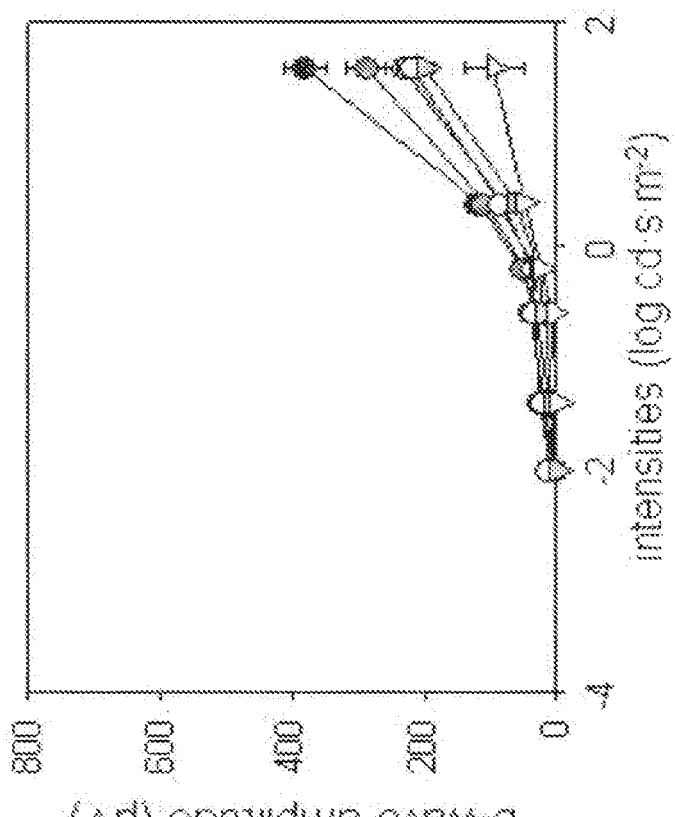
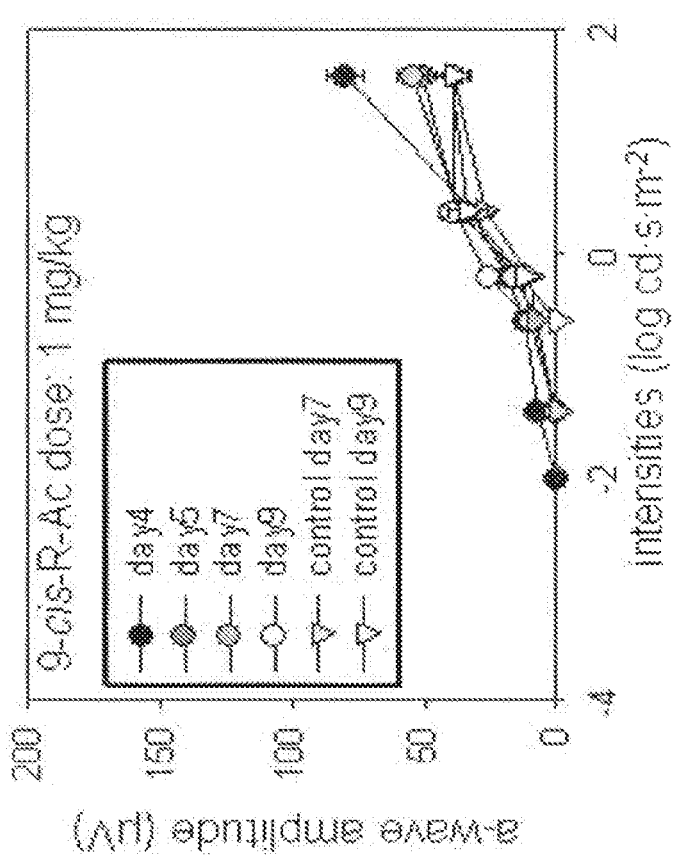
FIG. 6E
FIG. 6F

PHARMACEUTICAL FORMULATIONS COMPRISING 9-CIS-RETINYL ESTERS IN A LIPID VEHICLE

CROSS-REFERENCE TO RELATED APPLICATIONS

This application is a continuation of U.S. application Ser. No. 15/274,257, filed Sep. 23, 2016, which is a divisional of U.S. application Ser. No. 13/496,113, filed Mar. 14, 2012, which is a national stage application under 35 U.S.C. § 371 of International Application No. PCT/US2009/059126, filed Sep. 30, 2009, which claims the benefit of U.S. Patent Application No. 61/242,741, filed Sep. 15, 2009, under 35 U.S.C. § 119(e), which is incorporated herein by reference in its entirety. International Application PCT/US2009/059126 was published under PCT Article 21(2) in English.

BACKGROUND

Technical Field

This disclosure is related to pharmaceutical formulations comprising artificial retinoids, in particular, to stable formulations and dosage formulations suitable for visual chromophore replacement therapy.

Description of the Related Art

Visual perception results from a biological conversion of light energy into electrical signaling by retinal photoreceptors in the eye, a process called phototransduction. The phototransduction process is initiated by visual pigments, including the chromophore 11-cis-retinal bound to apoprotein G protein-coupled receptor opsins to form rhodopsin (Palczewski K. G protein-coupled receptor rhodopsin. *Annual review of biochemistry* 2006; 75:743-767). The chromophore absorbs photons, which triggers photoisomerization of the chromophore into its trans form and leads to signal transduction cascades (Palczewski K. supra; Ridge K D et al. Visual rhodopsin sees the light: structure and mechanism of G protein signaling. *J Biol Chem* 2007; 282:9297-9301). The isomerized chromophore, all-trans-retinal, is then reduced to all-trans-retinol, transported to the retina pigmented epithelium (RPE), and converted to fatty acid all-trans-retinyl esters by lecithin:retinol acyltransferase (LRAT). Finally, regeneration of 11-cis-retinal from the fatty acid all-trans-retinyl esters completes this retinoid (visual) cycle (see, e.g., U.S. Published Application Nos. 2004/0242704, 2006/028182, 2006/0221208).

Regeneration of 11-cis-retinal is critical for maintaining vision (Travis G H, et al. Diseases caused by defects in the visual cycle: retinoids as potential therapeutic agents. *Annu Rev Pharmacol Toxicol* 2007; 47:469-512). Defects in 11-cis-retinal production are associated with a number of inherited degenerative retinopathies (Gu S M, et al. Mutations in RPE65 cause autosomal recessive childhood-onset severe retina dystrophy. *Nature genetics* 1997; 17:194-197). Two examples are Leber congenital amaurosis (LCA), a childhood-onset retinal disease causing severe visual impairment; and retinitis pigmentosa (RP), another retinopathy with a more variable age of onset.

LCA is an inherited, severe, and currently incurable retinal degeneration that is a leading cause of blindness during childhood. At or soon after birth, LCA patients characteristically exhibit severe visual impairment evidenced by wandering nystagmus, amaurotic pupils, a pigmentary retinopathy with loss of cone and rod sensitivity, absent or greatly attenuated electroretinogram (ERG) responses and a ~100 folds decrease in cone flicker amplitude (Perrault I, et al. Leber congenital amaurosis. *Mol Genet Metab* 1999; 68:200-208; Fazzi E, et al. Leber's congenital amaurosis: an update. *Eur J Paediatr Neurol* 2003; 7:13-22; Fazzi E, et al. Response to pain in a group of healthy term newborns: behavioral and physiological aspects. *Functional neurology* 1996; 11:35-43).

RPE65, a 65 kDa protein specific to and abundant in the RPE that catalyses the isomerization of fatty acid all-trans-retinyl esters to 11-cis-retinol, is generally considered as the retinoid isomerase involved in the regeneration of 11-cis-retinal (Hamel C P, et al. Molecular cloning and expression of RPE65, a novel retinal pigment epithelium-specific microsomal protein that is post-transcriptionally regulated in vitro. *J Biol Chem* 1993; 268:15751-15757; Jin M, et al. Rpe65 is the retinoid isomerase in bovine retinal pigment epithelium. *Cell* 2005; 122:449-459; Moiseyev G, et al. RPE65 is the isomerohydrolase in the retinoid visual cycle. *Proceedings of the National Academy of Sciences of the United States of America* 2005; 102:12413-12418; Redmond T M, et al. Mutation of key residues of RPE65 abolishes its enzymatic role as isomerohydrolase in the visual cycle. *Proceedings of the National Academy of Sciences of the United States of America* 2005; 102:13658-13663). Mutations in the RPE65 gene account for up to 16% of LCA cases and 2% of autosomal recessive RP cases (Gu S M, supra; Marlhens F, et al. Mutations in RPE65 cause Leber's congenital amaurosis. *Nature genetics* 1997; 17:139-141; Morimura H, et al. Mutations in the RPE65 gene in patients with autosomal recessive retinitis pigmentosa or leber congenital amaurosis *Proceedings of the National Academy of Sciences of the United States of America* 1998; 95:3088-3093; Thompson D A, et al. Genetics and phenotypes of RPE65 mutations in inherited retinal degeneration, *Investigative ophthalmology & visual science* 2000; 41:4293-4299; Lorenz B, et al. Early-onset severe rod-cone dystrophy in young children with RPE65 mutations. *Investigative ophthalmology & visual science* 2000; 41:2735-2742). Spontaneous or engineered deletions of Rpe65 in mice and dogs result in 11-cis-retinal deficiency, an early-onset and slowly progressive retinal degeneration with dramatically reduced electroretinogram (ERG) responses and typical LCA pathology accompanied by accumulation of fatty acid all-trans-retinyl esters in the RPE (Redmond T M, et al. Rpe65 is necessary for production of 11-cis-vitamin A in the retinal visual cycle. *Nature genetics* 1998; 20:344-351; Pang J J et al. Retinal degeneration 12 (rd12): a new, spontaneously arising mouse model for human Leber congenital amaurosis (LCA). *Molecular vision* 2005; 11:152-162; Wrigstad A, et al. Ultrastructural changes of the retina and the retinal pigment epithelium in Briard dogs with hereditary congenital night blindness and partial day blindness. *Experimental eye research* 1992; 55:805-818; Acland G M, et al. Gene therapy restores vision in a canine model of childhood blindness. *Nature genetics* 2001; 28:92-95; Imanishi Y, et al. Noninvasive two-photon imaging reveals retinyl ester storage structures in the eye. *The Journal of cell biology* 2004; 164:373-383).

Several possible therapies for treating LCA are being investigated. RPE65 gene augmentation therapy and retinal prostheses have shown preliminary encouraging signs of visual rescue in early-stage clinical evaluations (Bainbridge J W, et al. Effect of gene therapy on visual function in Leber's congenital amaurosis. *The New England journal of medicine* 2008; 358:2231-2239; Maguire A M, et al. Safety and efficacy of gene transfer for Leber's congenital amaurosis. *The New England journal of medicine* 2008; 358: 2240-2248; Yanai D, et al. Visual performance using a retinal prosthesis in three subjects with retinitis pigmentosa. *American journal of ophthalmology* 2007; 143:820-827).

Recently, visual chromophore replacement therapy with 9-cis-retinal has been proposed as a novel pharmacological approach to bypass the defective retinoid cycle (Van Hooser J P, et al. Rapid restoration of visual pigment and function with oral retinoid in a mouse model of childhood blindness. *Proceedings of the National Academy of Sciences of the United States of America* 2000; 97:8623-8628; Van Hooser J P, et al. Recovery of visual functions in a mouse model of Leber congenital amaurosis. *J Biol Chem* 2002; 277:19173-19182; Alerman T S, et al. Impairment of the transient pupillary light reflex in Rpe65(−/−) mice and humans with leber congenital amaurosis. *Investigative ophthalmology & visual science* 2004; 45:1259-1271; Batten M L, et al. Pharmacological and rAAV Gene Therapy Rescue of Visual Functions in a Blind Mouse Model of Leber Congenital Amaurosis. *PLoS Med* 2005; 2:e333). 9-cis-retinal binds to opsin to form the rod cell pigment, iso-rhodopsin, which initiates phototransduction similarly to rhodopsin. It has been shown that oral administration of 9-cis-retinal or its precursors have regenerated opsin as iso-rhodopsin in the eyes, improved retinal function as assessed by ERG responses, and ameliorated the pupillary light reflex in Rpe65 and Lrat knockout mice, which are two genetic models of LCA. There is a need to further develop synthetic 9-cis-retinoids in orally-, gastric-, locally- (such as intravitreal), or intravenously-administered formulations for the treatment of various forms of inherited retinal degeneration caused by defects in the retinoid cycle.

BRIEF SUMMARY

Pharmaceutical formulations comprising artificial retinoids in a lipid vehicle are described. The artificial retinoids can be used to bypass critical blockades in the retinoid cycle, such as RPE65 deficiency or mutation, thereby generating an artificial cis-retinoid chromophore that can functionally combine with opsin. Also described are dosage formulations of the pharmaceutical formulations, including single, intermittent and daily dosing regimens.

Thus, one embodiment provides a pharmaceutical formulation comprising a lipid vehicle and one or more 9-cis-retinyl esters of Formula (I)

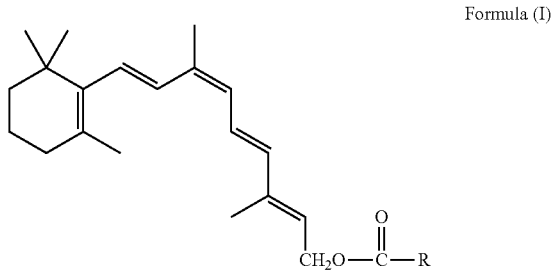

Formula (I)

wherein R is an alkyl group or an alkenyl group; and the lipid vehicle comprises more than 50 w/w % polyunsaturated fatty acids, the polyunsaturated fatty acids including an omega-6 fatty acid and an omega-3 fatty acid in a ratio (by weight) of less than 15.

In a particular embodiment, the 9-cis-retinyl ester of Formula (I) is 9-cis-retinyl acetate.

In a particular embodiment, the lipid vehicle comprises soybean oil.

A further embodiment provides a dosage formulation suitable for daily dosing of a 9-cis-retinyl ester to a subject in need thereof, the dosage formulation comprising about 1.25-20 mg/mL of 9-cis-retinyl acetate in soybean oil, wherein the dosage formulation provides about 1.25-40 mg/m$^2$ of the 9-retinyl acetate by body surface area of the subject over a 24-hour period.

Another embodiment provides a dosage formulation suitable for a single dosing by intravitreal administration of 9-cis-retinyl acetate to a subject, the dosage formulation comprising about 18-40% mg/mL of 9-cis-retinyl acetate in soybean oil.

A further embodiment provides a method of treating Leber congenital amaurosis in a human subject, comprising: administering a pharmaceutical formulation having an effective amount of one or more 9-cis-retinyl esters of Formula (I) in a lipid vehicle, the lipid vehicle comprising more than 50 w/w % polyunsaturated fatty acids, the polyunsaturated fatty acids including an omega-6 fatty acid and an omega-3 fatty acid in a ratio (by weight) of less than 15.

In a particular embodiment, the 9-cis-retinyl ester of Formula (I) employed in the method is 9-cis-retinyl acetate.

In a particular embodiment, the lipid vehicle employed in the method comprises soybean oil.

A further embodiment provides a method comprising administering, to a human subject deficient in 11-cis-retinal, a pharmaceutical formulation having an effective amount of one or more 9-cis-retinyl esters of Formula (I) in a lipid vehicle, the lipid vehicle comprising more than 50 w/w % polyunsaturated fatty acids, the polyunsaturated fatty acids including an omega-6 fatty acid and an omega-3 fatty acid in a ratio (by weight) of less than 15.

In a particular embodiment, the 9-cis-retinyl ester of Formula (I) employed in the method is 9-cis-retinyl acetate.

In a particular embodiment, the lipid vehicle employed in the method comprises soybean oil.

DETAILED DESCRIPTION OF THE INVENTION

Figure 1B:
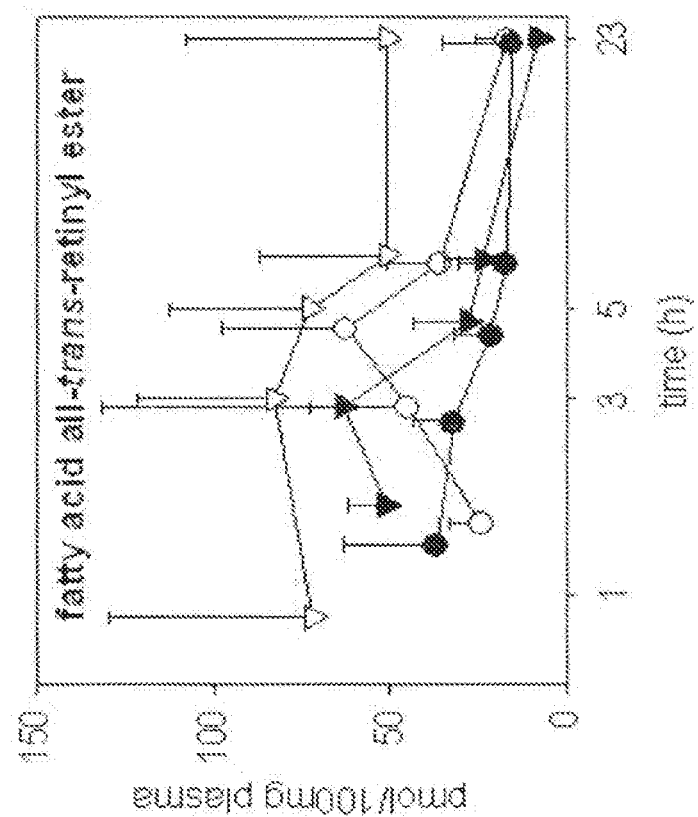
FIG. 1 (A-D) shows the relative absorptions of 9-cis-retinyl acetate in soybean oil and plasma retention of its active metabolites, including fatty acid 9-cis-retinyl esters and 9-cis-retinol.

Pharmaceutical formulations of 9-cis-retinyl esters suitable for retinoid replacement therapy are described. More specifically, the pharmaceutical formulation comprises one or more 9-cis-retinyl esters and a lipid vehicle.

As used herein, "retinoids" refers to a class of chemical compounds, natural or artificial, related to vitamin A. Structurally, retinoids share a common core structure composed of a cyclic end group, a conjugated polyene side chain and a polar end group. Naturally occurring retinoids include, for example, vitamin A (11-trans-retinol), 11-trans-retinal, and 11-trans-retinoic acid. Artificial or synthetic retinoids suitable for retinoid replacement therapy include, for example, 9-cis-retinyl esters, as defined herein, 9-cis-retinal and 9-cis-retinol.

As discussed herein, 9-cis-retinyl esters can act as precursors of a prodrug form or a prodrug of 9-cis-retinal, which is capable of functionally combining with opsins, thus completing the retinoid cycle despite, for example, RPE65 deficiency or mutation.

Thus, one embodiment describes a pharmaceutical formulation comprising: one or more 9-cis-retinyl esters and a lipid vehicle, the one or more 9-cis-retinyl esters being suspended in a lipid vehicle.

9-Cis-Retinyl Esters 9-cis-retinyl esters refer to the following generic structure of Formula (I):

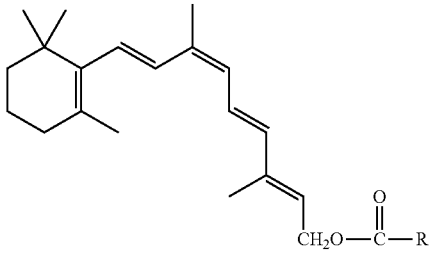

Formula (I)

wherein R is an alkyl group or an alkenyl group.

"Alkyl" refers to a straight or branched hydrocarbon chain radical consisting solely of carbon and hydrogen atoms, containing no unsaturation, having up to twenty two carbon atoms. In certain embodiments, an alkyl may comprise twelve to seventeen carbon atoms (also referred to as "$C_{12-17}$ alkyl"). In certain embodiments, an alkyl may comprise twelve to fifteen carbon atoms (also referred to as "$C_{12-15}$ alkyl"). In certain embodiments, an alkyl may comprise one to eight carbon atoms (also referred to as "$C_{1-8}$ alkyl"). In other embodiments, an alkyl may comprise one to six carbon atoms (also referred to as "$C_{1-6}$ alkyl"). In further embodiments, an alkyl may comprise one to four carbon atoms (also referred to as "$C_{1-4}$ alkyl"). The alkyl is attached to the rest of the molecule by a single bond, for example, methyl, ethyl, n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, an alkyl group may be optionally substituted by one or more of the following substituents: halo (including —F, —Br, —Cl and —I), cyano (—CN), nitro (—NO$_2$), oxo (=O), and hydroxyl (—OH).

"Alkenyl" refers to a straight or branched hydrocarbon chain radical consisting solely of carbon and hydrogen atoms, containing at least one unsaturation (i.e., C=C), having from two to up to twenty carbon atoms. In various embodiments, R is $C_{12-17}$ alkenyl, $C_{1-8}$ alkenyl, $C_{1-6}$ alkenyl or $C_{1-4}$ alkenyl. Unless stated otherwise specifically in the specification, an alkyl group may be optionally substituted by one or more of the following substituents: halo (including —F, —Br, —Cl and —I), cyano (—CN), nitro (—NO$_2$), oxo (=O), and hydroxyl (—OH).

In certain embodiments, the 9-cis-retinyl esters are artificial retinoids that act as precursors (i.e., pre-drugs) of a pro-drug form of 9-cis-retinal. More specifically, the 9-cis-retinyl esters can be converted by the liver to a metabolic pro-drug form, namely fatty acid 9-cis-retinyl esters, which are stored in the liver in hepatic lipid droplets. Fatty acid 9-cis-retinyl esters and retinol are mobilized from the liver and enter the circulation where they travel to the eye and RPE. There, they are converted to 9-cis-retinal which ultimately combines with photoreceptor opsins to form active visual pigments.

A preferred 9-cis-retinyl ester is 9-cis-retinyl acetate (i.e., R is methyl). Also referred to as "9-cis-R-Ac", 9-cis-retinyl acetate is a pharmaceutical pre-drug, which is metabolized by the liver to fatty acid 9-cis-retinyl esters, such as 9-cis-retinyl palmitate. Fatty acid 9-cis-retinyl esters and retinol are then converted to 9-cis-retinal in the eye and RPE as replacement of deficient chromophores such as 11-cis-retinal.

9-cis-R-Ac can be prepared by initially converting all-trans-retinyl acetate (Sigma-Aldrich) to a mixture of 9-cis-retinyl acetate and all-trans-retinyl acetate in the presence of a palladium catalyst (e.g., palladium salts, palladium oxides). The mixture of 9-cis-retinyl acetate and all-trans-retinyl acetate are then hydrolyzed to produce a mixture of 9-cis-retinol and all-trans-retinol. The pure 9-cis-retinol can be isolated by selective recrystallization and further esterified to pure 9-cis-R-Ac. A detailed description of the processes for preparing and purifying 9-cis-R-Ac can be found, for example, in GB Patent No. 1452012.

In other embodiments, the retinyl esters are pro-drugs (rather than precursors of pro-drugs) and can be directly converted to 9-cis-retinal in the eye and RPE. The pro-drug forms of the 9-cis-retinyl esters are typically fatty acid 9-cis-retinyl esters, in which R is a $C_{11-21}$ alkyl. As used herein, "fatty acid" refers to a carboxylic acid having a long aliphatic chain, which can be saturated (alkyl) or unsaturated (alkenyl). Typically, the aliphatic chain contains at least 11 carbons and can be as long as 21 carbons. Exemplary fatty acids include, without limitation, lauric acid, palmitic acid, palmitoleic acid, oleic acid, linoleic acid, and linolenic acid.

Thus, in one embodiment, R is a $C_{15}$ alkyl, and the 9-cis-retinyl ester of Formula (I) is 9-cis-retinyl palmitate.

In a further embodiment, R is a $C_{17}$ alkyl, and the 9-cis-retinyl ester of Formula (I) is 9-cis-retinyl stearate.

In other embodiment, R is a $C_{17}$ alkenyl, and the 9-cis-retinyl ester of Formula (I) is 9-cis-retinyl oleate.

The 9-cis-retinyl esters described herein can be prepared from 9-cis-retinol using appropriate esterifying agents in a manner similar to the preparation of 9-cis-R-Ac, the methods of which are within the knowledge of one skilled in the art.

As demonstrated herein, low doses (1 and 4 mg/kg) of an exemplary pre-drug 9-cis-R-Ac were found to be clinically safe and effective in maintaining visual function in Rpe65$^{-/-}$ mice as assessed by ERG recordings, retinoid levels in the eyes, retinal histology and vision-dependent behavioral studies. This compound is useful in treating, for example, humans with retinopathies stemming from inadequate retinoid chromophore generation.

Lipid Vehicles

Typically, the 9-cis-retinyl esters are oily substances and are lipophilic. Thus, the pharmaceutical formulation described may further comprise a lipid vehicle.

Because 9-cis-retinyl esters are light and oxygen-sensitive, their stability is critical to the efficacy and shelf-life of the formulation. A suitable lipid vehicle is therefore selected based on its ability to stabilize the 9-cis-retinyl esters suspended or solubilized therein.

As used herein, "lipid" or "lipid vehicle" refers to one or a blend of fatty acid esters. In various embodiments, the lipid vehicle comprises one or more triglycerides, which are formed when a single glycerol is esterified by three fatty acids. Triglycerides include both vegetable oils and animal fats.

In the context of describing the lipid vehicles, triglycerides are often simply referred to by their corresponding fatty acids. The fatty acids of the triglycerides can be saturated, monounsaturated and polyunsaturated, depending on the number of carbon-carbon double bond (C═C) in the aliphatic chains. A saturated fatty acid contains no carbon-carbon double bond in the aliphatic chain. Examples of saturated fatty acids include, e.g., palmitic and stearic acids. A monounsaturated fatty add contains a single carbon-carbon double bond (C═C) in the aliphatic chain. Examples of monounsaturated fatty acids include, e.g., oleic and palmitoleic acids. A polyunsaturated fatty acid contains at least two carbon-carbon double bonds in the aliphatic chain. Examples of polyunsaturated fatty acids include, e.g., linoleic acid (two C═C) and linolenic acid (three C═C). Further, the polyunsaturated fatty acids include omega-3 fatty acids and omega-6 fatty acids, depending on the location of the final C═C bond in the aliphatic chain. For example, linoleic is an omega-6 fatty acid, whereas linolenic is an omega-3 fatty acid.

Typically, the lipid vehicle is a blend of fatty acids, the relative amounts of each can impact the overall characteristics of the lipid vehicle, especially its ability to resist oxidation and to stabilize the 9-cis-retinyl ester suspended therein.

In certain embodiments, the lipid vehicle comprises more than 50 w/w % polyunsaturated fatty acids, the polyunsaturated fatty acids including an omega-6 fatty acid and an omega-3 fatty acid in a ratio (by weight) of less than 15. In specific embodiments, the lipid vehicle comprises triglyceride linoleate and triglyceride linolenate in a ratio (by weight) of less than 15, which collectively are more than 50% of the total weight of the lipid vehicle.

In other embodiments, the lipid vehicle can be a vegetable-based oil or oil blend that comprises more than 50 w/w % polyunsaturated fatty acids, the polyunsaturated fatty acids including an omega-6 fatty acid and an omega-3 fatty acid in a ratio (by weight) of less than 15.

Table 1 shows a number of vegetable oils and their fatty acid components in percentage weight (see, e.g., U.S. Published Application No. 2007071872).

TABLE 1

| Lipid Source | SAFA | MUFA ω7 + ω9 | PUFA ω6 | ω3 | ω6:ω3 | Total |
|---|---|---|---|---|---|---|
| Sunflower | 13 | 27 | 61 | 0.1 | 610 | 101.1 |
| Peanut | 14 | 43 | 35 | 0.1 | 350 | 92.1 |
| Grapeseed | 14 | 21 | 68 | 0.5 | 136 | 103.5 |
| Corn | 16 | 32 | 51 | 1 | 51 | 100 |
| Palm | 51 | 40 | 9 | 0.25 | 36 | 100.25 |
| Olive (1) | 16 | 70 | 13 | 0.6 | 22 | 100.6 |
| Coconut | 92 | 7 | 1.5 | 0.1 | 15 | 100.6 |
| Olive (2) | 15 | 79 | 5 | 0.6 | 8 | 99.6 |
| Wheat germ | 20 | 18 | 55 | 7 | 8 | 100 |
| Soybean | 16 | 22 | 54 | 7.5 | 7 | 99.5 |
| Walnut | 11 | 15 | 62 | 12 | 5 | 100 |
| Canola | 7 | 63 | 20 | 10 | 2 | 100 |
| Chia | 9.7 | 6.7 | 19 | 64 | 0.3 | 99.4 |
| Flax | 6.9 | 19.5 | 15 | 57.5 | 0.26 | 98.9 |
| Perilla | 8.5 | 14.4 | 12.6 | 63.2 | 0.20 | 98.7 |

SAFA = Saturated fatty acids
MUFA = Monosaturated fatty acids
PUFA = Polyunsaturated fatty acids
ω6:ω3 = ratio of omega-6 to omega-3 polyunsaturated fatty acids.

Soybean oil is a suitable lipid vehicle as it comprises about 62% of polyunsaturated fatty acid (54% linoleic and 8% linolenic), 25% monounsaturated fatty acid (oleic), and 16% saturated fatty acid (11% palmitic acid, and 5% stearic acid).

Soybean oil is a clear and odorless oil that is miscible with the 9-cis-retinyl esters described herein. When compared to fatty acids containing lower concentration of polyunsaturated fatty acids (e.g., Canola oil and olive oil, which contains about 30% and less than 20% polyunsaturated fatty acids, respectively), soybean oil unexpectedly exhibits superior stabilizing effect, as evidenced by the higher contents of pure 9-cis-retinyl acetate retained in the formulations following a two-week period.

In addition, when compared to fatty acids that have a higher ratio of omega-6 to omega-3 polyunsaturated fatty acid, soybean oil also exhibits superior stabilizing effect. For example, sunflower oil, although having a total amount of polyunsaturated fatty acids (61%) comparable to that of soybean oil, has a much higher ratio of omega-6 to omega-3 polyunsaturated fatty acid (over 600) than soybean oil (about 7). As shown in Table 2 (Example 1), the stabilizing effect of sunflower oil is comparable to that of Canola oil, both are much lower than soybean oil (USP grade).

Significantly, the soybean oil formulations are most stable as compared to formulations of other vehicles at temperatures close to physiological conditions (e.g., 40° C.). Highly refined soybean oil that meets the U.S.P. monograph is preferred (e.g., as provided by Spectrum Chemicals) as it was observed that U.S.P. grade soybean oil provides enhanced stabilization than commercial grade soybean oil (see, Example 1).

Furthermore, the soybean oil vehicle provides the highest plasma level of the metabolites of 9-cis-retinyl esters. FIG. 1 shows the relative absorptions of 9-cis-R-Ac and plasma retention of its active metabolites, fatty acid 9-cis-retinyl esters and 9-cis-retinol.

It is thus demonstrated that soybean oil confers both stability of 9-cis-retinyl esters and high plasma retention of the active metabolites of the same, thereby providing synergistic benefits to the formulations.

In a further embodiment, the lipid vehicle is walnut oil, which comprises 72% polyunsaturated fatty acids (62% linoleic and 12% linolenic).

In yet another embodiment, the lipid vehicle is wheat germ oil, which comprises 62% polyunsaturated fatty acids (55% linoleic and 7% linolenic).

Formulations

In general, the pharmaceutical formulations can include any of the 9-cis-retinyl ester described herein combined with a suitable lipid vehicle.

One embodiment describes a pharmaceutical formulation comprising one or more 9-cis-retinyl esters in a lipid vehicle, wherein the lipid vehicle comprises more than 50 w/w % polyunsaturated fatty acids, the polyunsaturated fatty acids including an omega-6 fatty acid and an omega-3 fatty acid in a ratio (by weight) of less than 15.

A further embodiment describes a pharmaceutical formulation comprising 9-cis-retinyl acetate in a lipid vehicle, wherein the lipid vehicle comprises more than 50 w/w % polyunsaturated fatty acids, the polyunsaturated fatty acids including an omega-6 fatty acid and an omega-3 fatty acid in a ratio (by weight) of less than 15.

A further embodiment describes a pharmaceutical formulation comprising 9-cis-retinyl acetate in a lipid vehicle, wherein the lipid vehicle comprises triglyceride linoleate and triglyceride linolenate in a ratio (by weight) of less than 15, which collectively are more than 50% of the total weight of the lipid vehicle.

A further embodiment describes a pharmaceutical formulation comprising 9-cis-retinyl acetate in soybean oil.

Yet another embodiment describes a pharmaceutical formulation comprising 9-cis-retinyl acetate in walnut oil.

Yet another embodiment describes a pharmaceutical formulation comprising 9-cis-retinyl acetate in wheat germ oil.

In various embodiments, the pharmaceutical formulation comprises up to 40% (by weight) 9-cis-retinyl esters, up to 30% (by weight) 9-cis-retinyl esters, up to 25% (by weight) 9-cis-retinyl esters, up to 10% (by weight) 9-cis-retinyl esters, up to 5% (by weight) 9-cis-retinyl esters.

Optional Components

The pharmaceutical formulations described herein can optionally comprise additional components which enhance stability and palatability. For example, one or more stabilizer (e.g., an anti-oxidant) may be included to impart further stabilizing effect. Further, flavoring agents may be added to orally-administered formulations to improve the taste.

The anti-oxidant employed in the present disclosure may be one or more of the following: α-tocopherol, butylated hydroxyanisole (BHA), butylated hydroxytoluene (BHT), ascorbyl palmitate and propyl gallate, tert-butyl hydroquinone (TBHQ), Chelating agents such as disodium edetate and calcium disodium edentate may be employed.

Flavoring agents and flavor enhancers make the pharmaceutical formulations more palatable to the patient. Common flavoring agents and flavor enhancers for pharmaceutical products that may be included in the composition of the present invention include maltol, vanillin, ethyl vanillin, menthol, citric acid, fumaric acid, ethyl maltol, and tartaric acid. Flavored oils (e.g., lemon oil) are preferred as they are miscible with the lipid vehicle. Sweetening agents such as sorbitol, saccharin, sodium saccharin, sucrose, aspartame, fructose, mannitol and invert sugar may be added to improve the taste.

Water, surfactants or emulsifiers can be added to the oil-based formulations to form a mixture suitable for oral administration (e.g., in the form of a beverage) or intravenous injection. Suitable surfactants and emulsifiers include, for example, soy lecithin and dipalmitoylphosphatidyl choline. Beverages, such as soy milk, can also be added directly to the formulations described herein.

Thus, one embodiment provides a beverage comprising one or more 9-cis-retinyl esters and a lipid vehicle, wherein the lipid vehicle comprises more than 50 w/w % polyunsaturated fatty acids, the polyunsaturated fatty acids including an omega-6 fatty acid and an omega-3 fatty acid in a ratio (by weight) of less than 15.

A further embodiment provides a drinkable formula, emulsion or beverage comprising 9-cis-retinyl acetate, soybean oil and a drinkable liquid medium. In certain embodiments, the drinkable liquid medium is in the form of oil-in-water emulsion (e.g., milk or soy milk). Additional emulsifiers, such as acacia, tragacanth gums, and methyl cellulose, can also be employed.

A further embodiment provides an oral formulation in the form of capsules, the capsules containing 9-cis-retinyl acetate, soybean oil. Additional excipients such as anti-oxidants can be included, as is recognized by one skilled in the art.

Administration and Dosage Formulations

The pharmaceutical formulation described herein can be administered to a subject by oral, gastric or local administration such as intravitreal injection and intravenous injection.

Oral administration can be effected by oral gavage, or via a drinkable formula or beverage which includes one or more 9-cis-retinyl esters, a lipid vehicle and a beverage such as soymilk.

Gastric administration can be effected by gastric gavage (e.g., stomach tube).

Local administration such as intravitreal (through the eye) injection and intravenous injection are carried out with syringes.

As used herein, a "subject" refers to a patient, may be from any mammalian species, e.g. primates, particularly humans; rodents, including mice, rats, and hamsters; rabbits; equines; bovines; canines; felines; etc. Animal models, in particular, genetically manipulated animals, are of interest for experimental investigations, providing a model for treatment of human diseases, e.g., LCA.

Typically, all doses of 9-cis-R-Ac are completely miscible in the lipid vehicles, including soybean oil, USP (Spectrum Chemicals). In various embodiments, single, intermittent and daily administrations are described. Further, based on the post-absorptive levels of their pharmacologically active metabolites in plasma, the dosage and corresponding efficacy of the 9-cis-retinyl esters can be assessed by using ERG, visual acuity, full-field stimulus testing, visual field analysis, color vision testing.

As shown in the Examples, a dose-dependent improvement of both the level and duration of retinal function were observed in Rpe65 and Lrat knockout mice, which are two genetic models of LCA. Importantly, pharmacological activity was sustained for sufficiently long periods after dosing to enable formulation of a flexible, intermittent dosing schedule.

More specifically, single doses of 9-cis-R-Ac (6.25-50 mg/kg) led to significant dose-dependent improvement of ERG responses. Daily doses (1, 4 and 12.5 mg/kg) for two weeks were well tolerated and induced remarkable improvement of retinal function. Significant dose-dependent improvements of ERG responses were observed 6 days after administration of 9-cis-R-AC daily for 3 days at 1, 4 and 12.5 mg/kg. Mice given either daily or intermittent 9-cis-R-Ac treatment at 1 and 4 mg/kg/day and evaluated two months later displayed dose-dependent improvement of retinal function and morphology 8 weeks later whereas retinal function deteriorated in comparable 3-month-old control animals.

Thus, in one embodiment, described herein is a dosage formulation suitable for 24 hour or daily dosing of a 9-cis-R-Ac to a subject in need thereof comprising about 1.25-20 mg/mL 9-cis-R-Ac in soybean oil, wherein the dosage formulation provides about 1.25-40 mg/m$^2$ of the 9-cis-R-Ac by body surface area of the subject over a 24-hour period.

In another embodiment, the dosage formulation provides a time to maximum or peak plasma concentration of 9-cis-retinyl esters at about 3-6 hours following oral or gastric administration of the dosage formulation. As used herein, "peak plasma concentration" is a pharmacokinetic measure for assessing bioavailability of a pharmaceutical product. Plasma drug concentration increases with extent of absorption; the peak is reached when drug elimination rate equals absorption rate. In addition to the maximum (peak) plasma drug concentration, the corresponding peak time (when maximum plasma drug concentration occurs), and area under the plasma concentration-time curve are also parameters of pharmacokinetics.

In a further embodiment, described herein is a dosage formulation suitable for a single dosing by intravitreal administration of 9-cis-retinyl acetate to a subject, the dosage formulation comprising about 18-40% mg/mL of 9-cis-retinyl acetate in soybean oil. It has been found that a single dosage for intravitreal administration can last for days, even weeks in the subject's eye, possibly through a manner of sustained release.

Use of 9-Cis-Retinyl Esters as Retinoid Replacement Therapies

Also described herein are methods of using 9-cis-retinyl esters of Formula (I) as retinoid replacement therapies for retinal degeneration in humans.

Appropriate animal models for evaluating the efficacy and safety of the 9-cis-retinyl esters as retinoid replacement therapies were carried out (see, Examples). The animal models used are Rpe65$^{-/-}$ mice, which lack retinal pigmented epithelium-specific 65 kDa protein (RPE65) and develop retinopathy and blindness resembling LCA in humans.

The pharmacokinetic and pharmacodynamic effects of the pre-drug indicate that the pre-drug is converted to a pro-drug in the liver, i.e. to mostly 9-cis-retinyl palmitate, in the Rpe65$^{-/-}$ mouse model (see, Examples). Further, in the in the Rpe65$^{-/-}$ mouse model, 9-cis-retinoids were observed to have been delivered to the retina in two ways, i.e. primarily and promptly from the circulating blood and secondarily and more slowly from 9-cis-retinoids stored in the liver (see, Example 5).

By using several different regimens in Rpe65$^{-/-}$ mice to evaluate drug efficacy and safety, it is demonstrated that 9-cis-retinyl esters can be used as synthetic retinoids to treat human LCA patients. Both dose- and administration period-dependent retention of visual function were observed, even at the lowest 1 and 4 mg/kg doses tested (FIGS. 2, 4, 6, 8). Significantly, a dose-dependent prolongation of efficacy was observed for the pre-drug 9-cis-R-Ac.

Thus, one embodiment provides a method of treating Leber congenital amaurosis in a human subject, comprising administering a pharmaceutical formulation having an effective amount of one or more 9-cis-retinyl esters of Formula (I) in soybean oil. In a more specific embodiment, the 9-cis-retinyl esters of Formula (I) is 9-cis-retinyl acetate.

A further embodiment provides a method comprising: administering, to a human subject deficient in 11-cis-retinal, a pharmaceutical formulation having an effective amount of one or more 9-cis-retinyl esters of Formula (I) in soybean oil In a more specific embodiment, the 9-cis-retinyl esters of Formula (I) is 9-cis-retinyl acetate.

The various embodiments described herein are further illustrated by the following non-limiting examples.

EXAMPLES

Materials, Methodology and Analysis

Electroretinogram (ERG)—ERGs were recorded on anesthetized mice as described in, e.g., Maeda A, et al. Role of photoreceptor-specific retinol dehydrogenase in the retinoid cycle in vivo. *J Biol Chem* 2005; 280:18822-18832; and Maeda T, et al. A Critical Role of CaBP4 in the Cone Synapse. *Investigative ophthalmology & visual science* 2005; 46:4320-4327.

Briefly, mice first were dark-adapted overnight prior to recording. Then under a safety light, mice were anesthetized by intraperitoneal injection of 20 µl/g body weight of 6 mg/ml ketamine and 0.44 mg/ml xylazine diluted with 10 mM sodium phosphate, pH 7.2, containing 100 mM NaCl. Pupils were dilated with 1% tropicamide. A contact lens electrode was placed on the eye and a reference electrode and ground electrode were positioned on the ear and tail, respectively. ERGs were recorded with the universal testing and electrophysiologic system (UTAS) E-3000 (LKC Technologies, Inc.).

Single-flash recording—White light flash stimuli were employed with a range of intensities (from −3.7 to 2.8 log cd·s·m$^{-2}$), and flash durations were adjusted according to intensity (from 20 µs to 1 ms). Two to five recordings were made at sufficient intervals between flash stimuli (from 10 s to 10 min) to allow mice to recover. Typically, four to eight animals were used for recording each point. The one-way ANOVA test was used for statistical analysis of responses.

Histology and Immunohistochemistry—Histological procedures employed for the eye analyses as described in Maeda A, et al. supra.

Analyses of Retinoic Acid and Non-polar Retinoids—All experimental procedures related to extraction, retinoid derivatization and separation of retinoids were done under dim red light provided by a Kodak No. 1 safelight filter (transmittance>560 nm). Retinoic acid extraction from liver was performed as formerly described in, e.g., Batten M L. et al. supra. Analyses of polar retinoids in plasma, eye and liver were performed with an Agilent 1100 HPLC and two tandem normal phase columns: a Varian Microsorb Silica 3 μm, 4.6×100 mm (Varian, Palo Alto, Calif.) and an Ultrasphere-Si, 5 μm, 4.6×250 mm column (Aleman T S, et al. supra). An isocratic normal phase system of hexane: 2-propanol:glacial acetic acid (1000:4.3:0.0.675; v/v/v) was used for elution at a flow rate of 1 ml/min at 20° C. with detection at 355 nm. Calibration was done with standards of all-trans-retinoic acid and 9-cis-retinoic acid purchased from Sigma-Aldrich. Analyses of non-polar retinoids in plasma, eye and liver were carried out by normal phase HPLC (Ultrasphere-Si, 5 μm, 4.6×250 mm, Beckman, Fullerton, Calif.) with 10% ethyl acetate and 90% hexane at a flow rate of 1.4 ml/min with detection at 325 nm by an HP1100 HPLC with a diode array detector and HP Chemstation A.03.03 software.

Example 1

Stability Tests of Various Formulations

Several different lipid-based formulations of 9-cis-R-Ac were prepared to test the stability conferred by various lipid vehicles. As 9-cis-R-Ac was considered light sensitive, amber vials were used whenever possible and the compound was handled under gold fluorescent light. 9-cis-R-Ac was removed from the −20° C. freezer and warmed to room temperature for 30 minutes. Compound handling was performed under a flow of Argon gas as the compound was transferred into pre-weighed amber vials and re-weighed to calculate the amount of compound before the vials were backfilled with argon and stored at −20° C. until use.

Mixtures of 9-cis-R-Ac (1.4 to 8 mg/mL) in the various carriers/vehicles were prepared using the amber vials containing accurately weighed compound. The sample vials were backfilled with argon and mixed by vortexing. The polyoxyl 35 caster oil samples were heated to 60° C. Each sample was divided into two portions and stored at 4° C. or 40° C. The samples were analyzed by HPLC for 9-cis-retinyl acetate content following preparation (day 0), and at time points up to 2 weeks.

Samples for HPLC analysis were diluted to approximately 0.1 mg/mL in THF. Samples were analyzed immediately or stored at −20° C. or −70° C. for up to 1 week until analysis. Percent recovery was calculated relative to the formulation concentration at day 0 by HPLC.

Unexpectedly, soybean oil (USP), with and without BHT, provides the most stable suspension for 9-cis-R-Ac, particularly at physiological temperature (about 40° C.), as indicated by the percentage amount of the 9-cis-R-Ac content in the formulation at Day 7 and Day 14 (Table 2).

TABLE 2

|  | Stability | | | |
|---|---|---|---|---|
|  | 4° C. | | 40° C. | |
| Vehicle | Day 7 | Day 14 | Day 7 | Day 14 |
| Canola oil | 100% | 99% | 95% | 89% |
| Rapeseed oil | 102% | 102% | 95% | 88% |
| Sunflower seed oil | 99% | 99% | 91% | 87% |
| Clove leaf oil | 96% | 93% | 16% | 6% |
| Olive oil | 99% | 97% | 91% | 89% |
| Eugenol | 95% | 90% | 6% | 2% |
| Soybean oil | 107% | 101% | 93% | 69% |
| Soybean oil, USP | 103% ± 1% | 101% ± 1% | 99% ± 2% | 98% ± 1% |
| with 0.1% w/v BHT | 107% ± 1% | 104% ± 1% | 103% ± 1% | 97% ± 1% |
| with 0.1% w/v alpha tocopherol | 104% ± 2% | 102% ± 1% | 101% ± 1% | 94% ± 0% |
| Polyoxyl 35 castor oil | 101% ± 1% | 98% ± 2% | 95% ± 1% | 89% ± 2% |
| 25% Polyoxyl 35 castor oil in water | 100% ± 1% | 98% ± 1% | 80% ± 1% | 66% ± 1% |

Example 2

Plasma Retention of 9-Cis-Retinyl Acetate Metabolites

Several different oil-based preparations were prepared to test the absorption levels of 9-cis-R-Ac in plasma. More specifically, a single 50 mg/kg dose of 9-cis-retinyl acetate (50 mg/kg) suspended in 4 different vehicle oils was administrated by gastric gavage to 5-week-old C57/Bl6 mice and retinoid levels were determined in the plasma thereafter (n=5 for each time point per group).

Figure 1A:
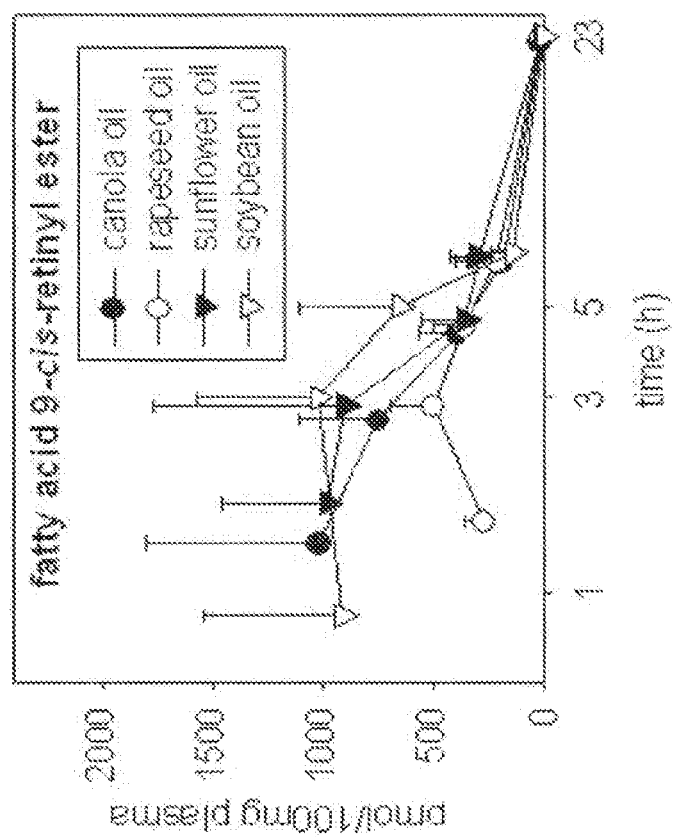
Figure 1D:
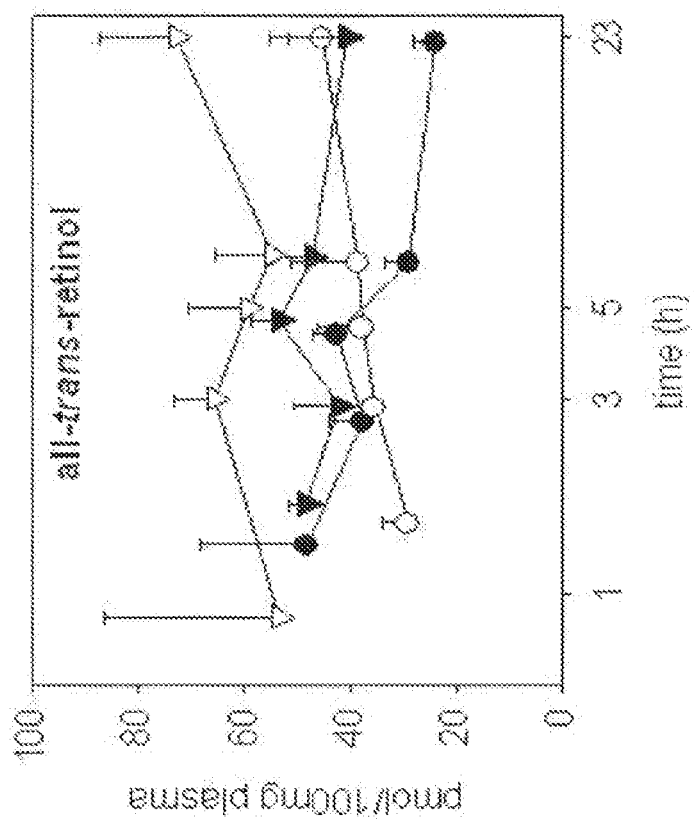
Figure 1C:
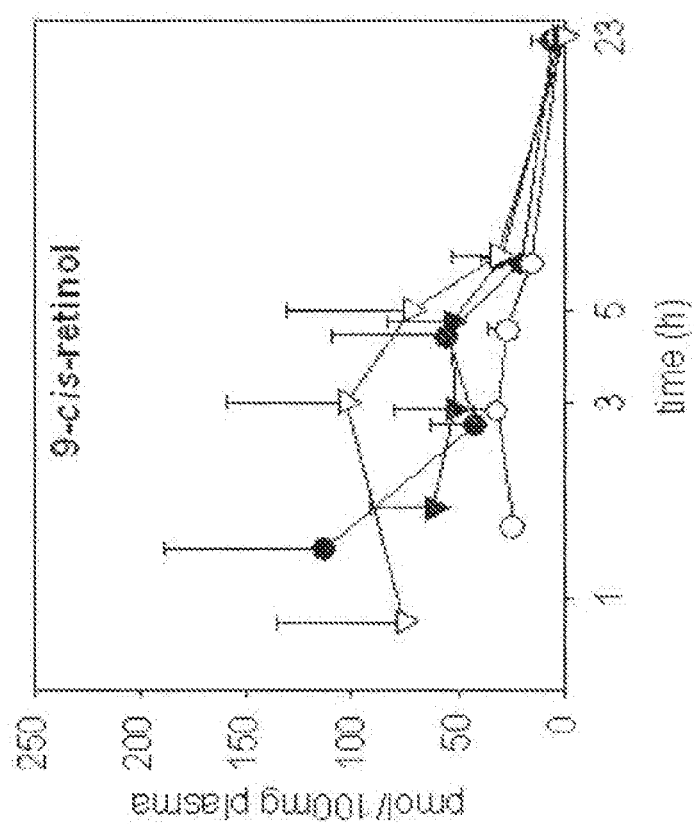

Solution of 9-cis-R-Ac in either soybean oil or sunflower oil, as compared to canola and rapeseed oils, provided the best absorption of 9-cis-R-Ac as evidenced by the highest plasma levels of fatty acid 9-cis-retinyl esters and 9-cis-retinol, both active metabolites of 9-cis-R-Ac (FIG. 1A, C, 11). The highest plasma levels of these 9-cis-retinoids were noted at ∼3 h. Plasma levels of all-trans-retinol and fatty acid all-trans-retinyl esters did not differ significantly, either among the test vehicles did or during the 23 h test period, suggesting that cis-retinoids were not converted to all-trans-retinoids (FIG. 1B, D).

Figure 10:
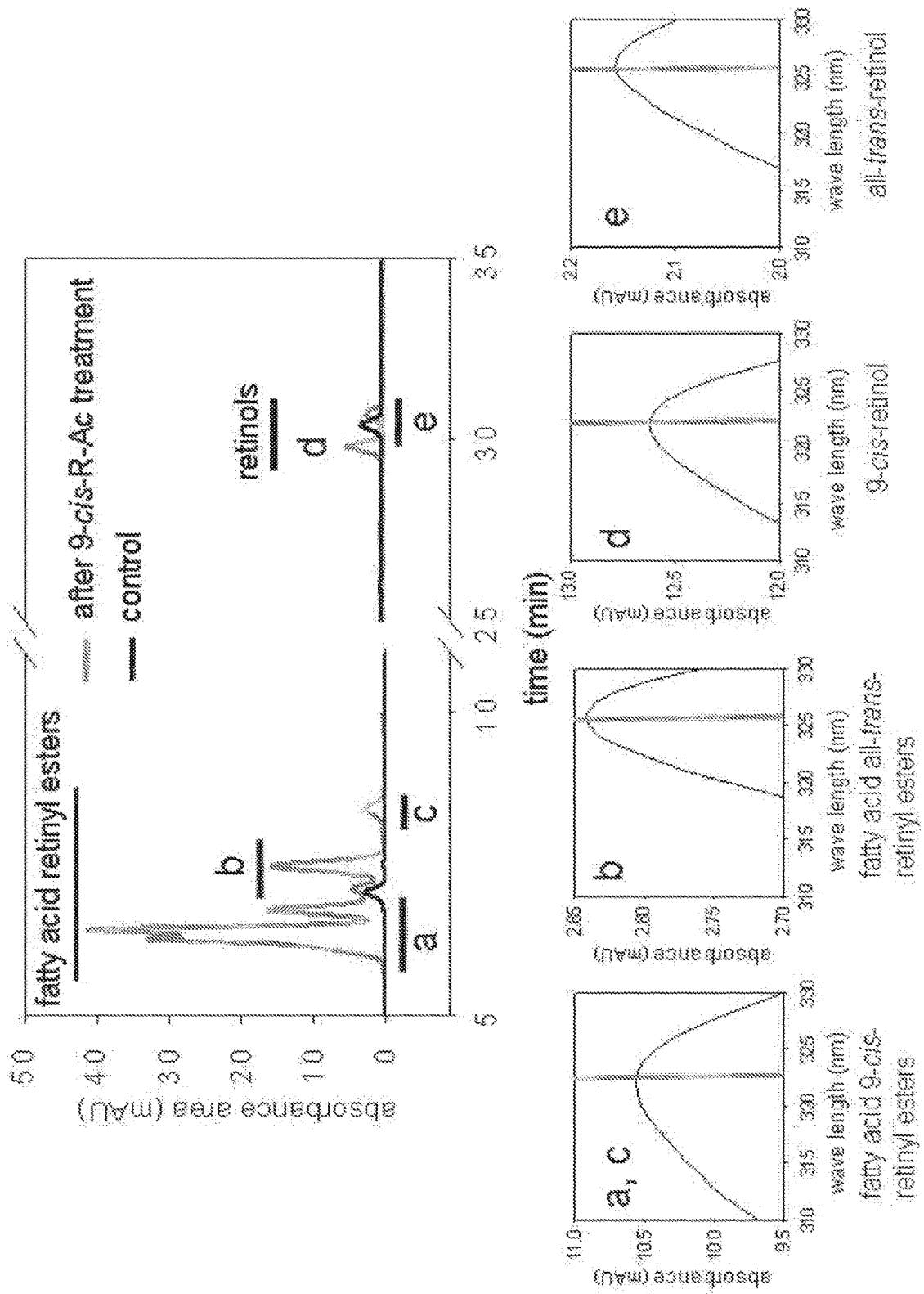
FIG. 10 shows the plasma levels of retinoids as determined by HPLC after 9-cis-retinyl acetate administration.

FIG. 10 shows the retinoids in plasma as determined by HPLC. Fatty acid retinyl esters detected early in the elution phase (a, b, c) consisted of four peaks of 9-cis (a, c) and two peaks of all-trans (b) isomers. Both 9-cis-retinol (d) and all-trans-retinol (e) eluted later.

Example 3

Effects of Single Doses of 9-Cis-R-Ac on Retinal Function of Rpe65$^{-/-}$ Mice Single doses (2-50 mg/kg) of 9-cis-R-Ac in soybean oil were administered to 5-week-old Rpr65Rpe65$^{-/-}$ mice to test whether the pre-prodrug 9-cis-R-Ac was capable of delivering artificial chromophore to the eye.

Mice showed no obvious clinical side effects, even after receiving the highest dosing of 50 mg/kg. Following dark-adaption for 3 days post-gavage, scotopic single flash ERGs were recorded and eyes were collected to assess 9-cis-retinal levels.

Figure 2A:
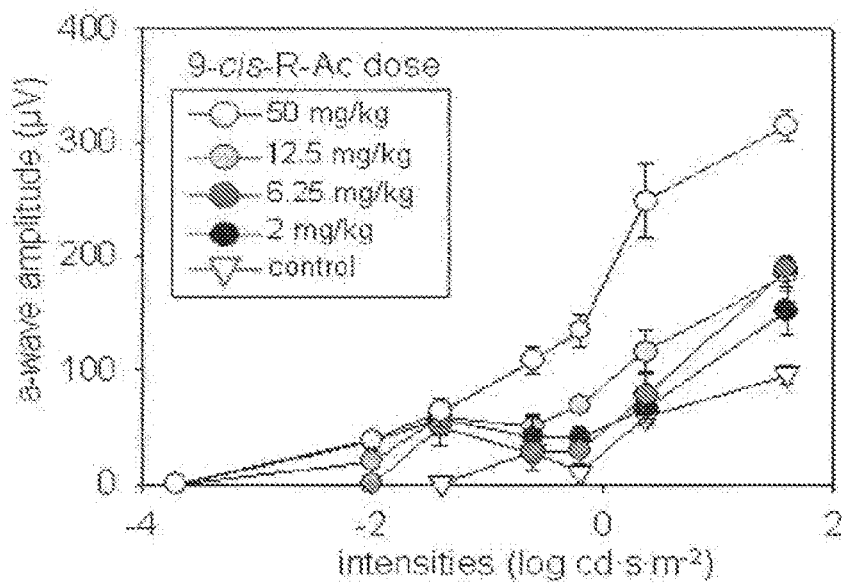
FIG. 2 (A-C) shows a dose-dependent increase in both a-wave and b-wave amplitudes in mice treated with a single dose of 9-cis-retinyl acetate in soybean oil.
Figure 2B:
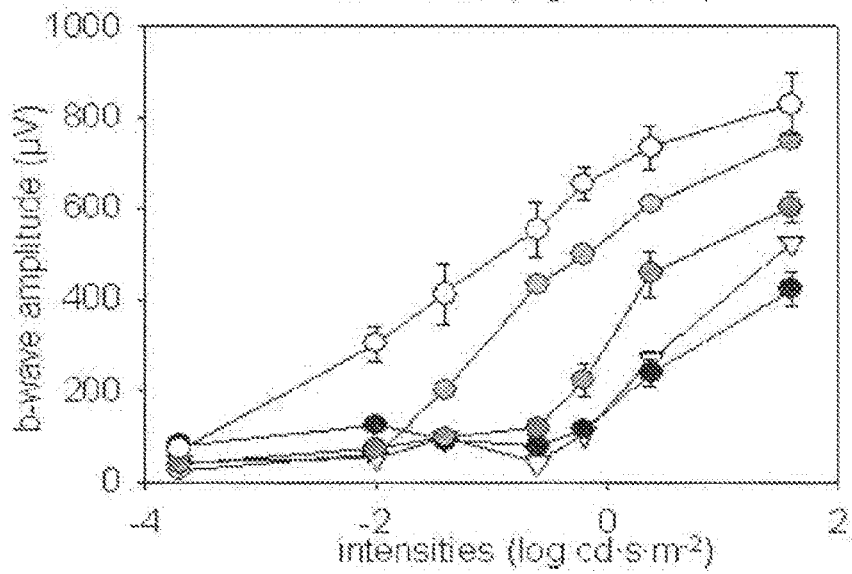
Figure 2C:
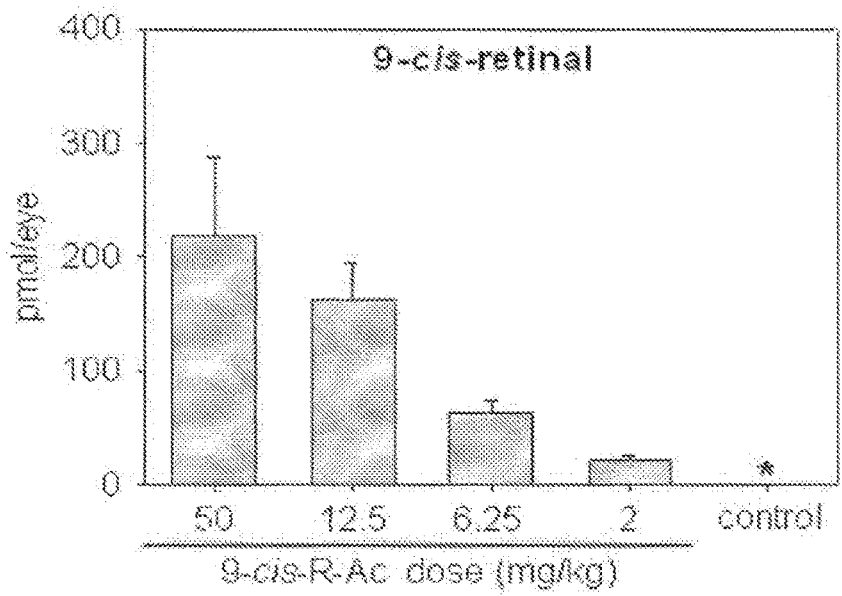

Scotopic ERGs of the treated mice showed a dose-dependent increase in both a-wave and b-wave amplitudes (FIG. 2A, B); the lowest tested dose that provided significant improvement after high intensity stimuli was 6.25 mg/kg. Similarly, a dose-dependent accumulation of 9-cis-retinal was found in the eyes of treated mice that correlated with improvement in retinal function (FIG. 2C). No fatty acid 9-cis-retinyl esters were detected in any of the analyzed eyes whereas levels of fatty acid all-trans-retinyl esters ranged from ~1 to 1.6 nmol/eye and did not differ significantly among the four treatment groups. Moreover, fatty acid all-trans-retinyl ester levels were similar to the 1.2 nmol/eye reported for untreated 5-week-old Rpe65$^{-/-}$ mice.

9-cis-Retinol (43 pmol/eye) was detected only in the eyes of mice dosed with 50 mg/kg, whereas all-trans-retinol levels, varying from 14 to 22 pmol/eye, did not differ significantly among the four treatment groups. No 11-cis-retinoids were detected in any of the eyes.

Thus, the results suggest that 9-cis-retinal recombine with opsin to form iso-rhodopsin. Importantly, lower doses of 9-cis-R-Ac (2 and 4 mg/kg) induced positive ERG effects even though only trace levels of 9-cis-retinal were detected in the eye (FIG. 2).

Example 4

Effects of 9-Cis-R-Ac Given Daily for 14 Days

Figure 3:
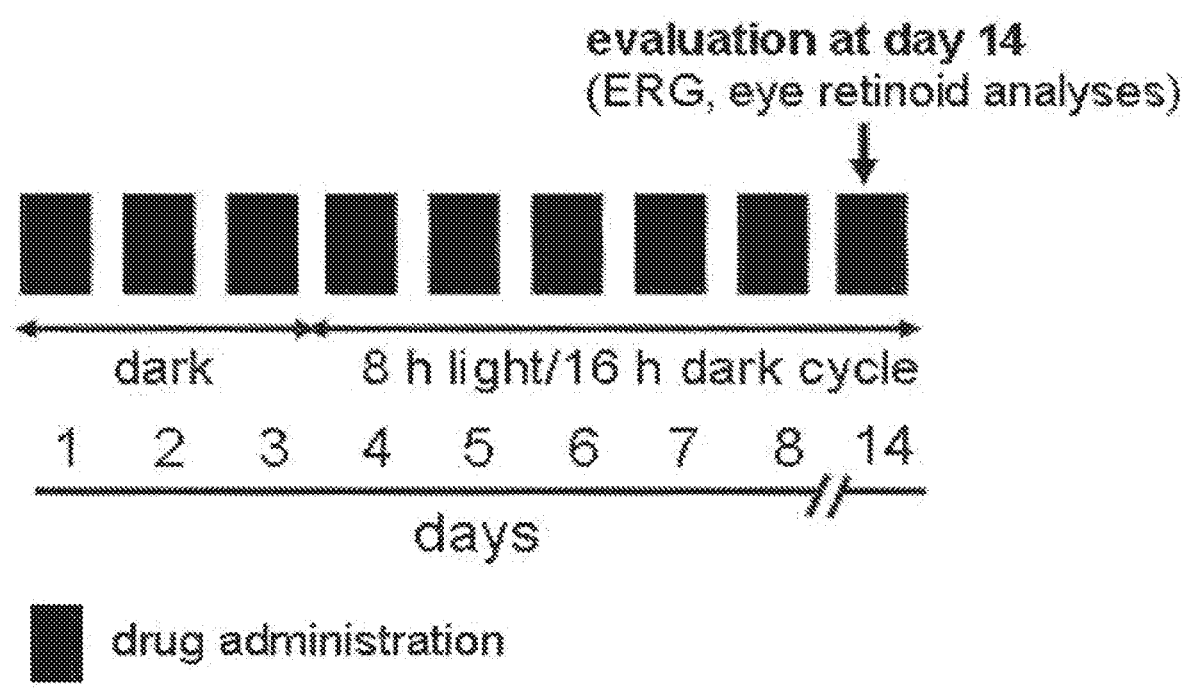
FIG. 3 shows a dosing regimen during a 14-day period in which single-flash ERGs were recorded and retinoid levels in the eyes were measured.

The retinal function of Rpe65$^{-/-}$ and C57Bl/6 mice were tested after repeated daily dosing of 9-cis-R-Ac. To test this directly, 5-week-old Rpe65$^{-/-}$ mice were gavaged daily with 9-cis-R-Ac in soybean oil at doses of 1, 4, or 12.5 mg/kg for 14 days. The mice were exposed to an alternating dark and fluorescent light (luminance range of 500-1500 lux) environment during the last 11 days of treatment. Scotopic single-flash ERGs were recorded and retinoid levels in the eyes were measured (FIG. 3).

Figure 4B:
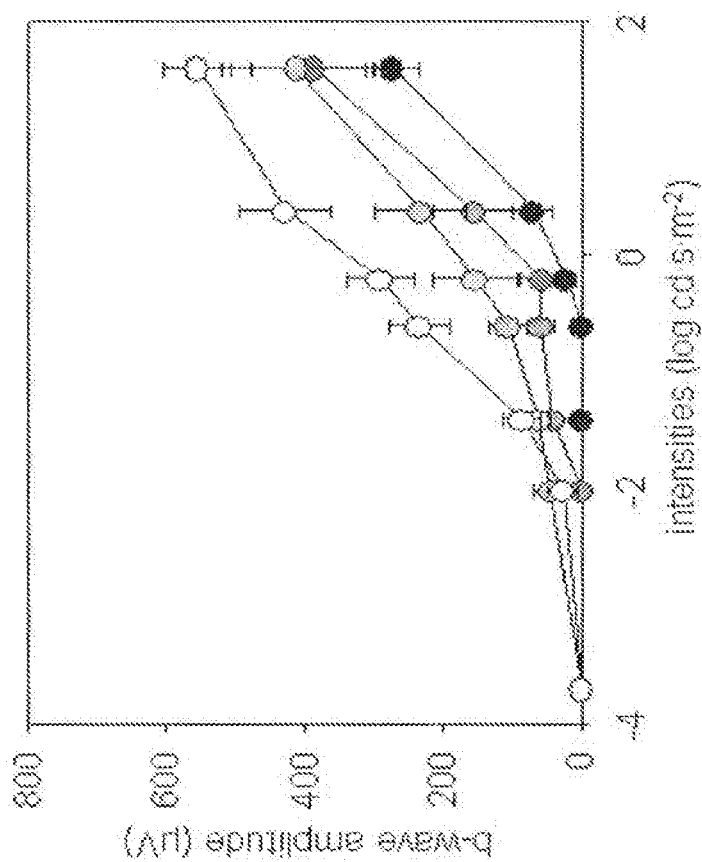
FIG. 4 (A-D) shows ERGs in a dose-dependent increase in the amplitudes of both a- and b-waves in treated as compared to baseline 5-week-old Rpe65$^{-/-}$ mice.
Figure 4A:
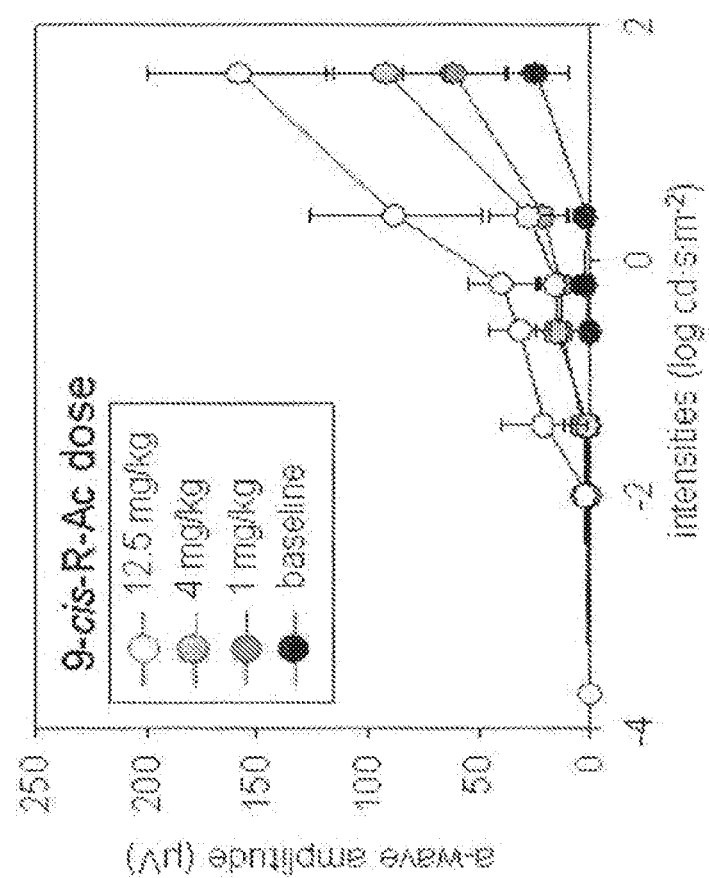

ERGs showed a dose-dependent increase in the amplitudes of both a- and b-waves in treated as compared to baseline 5-week-old Rpe65$^{-/-}$ mice (FIG. 4A, B). Even the lowest daily test dose of 1 mg/kg evoked a significant improvement in retinal function as compared to the control group.

Figure 4D:
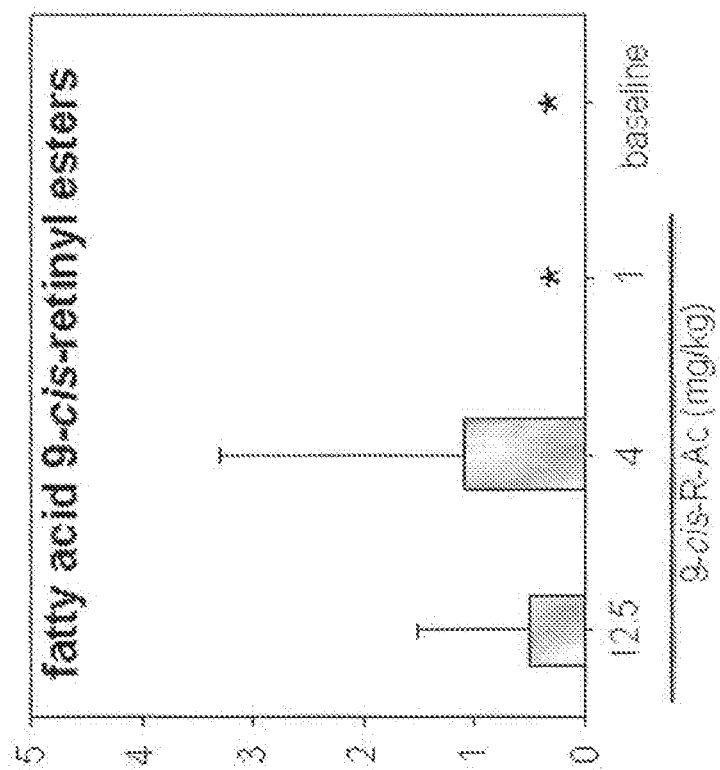
Figure 4C:
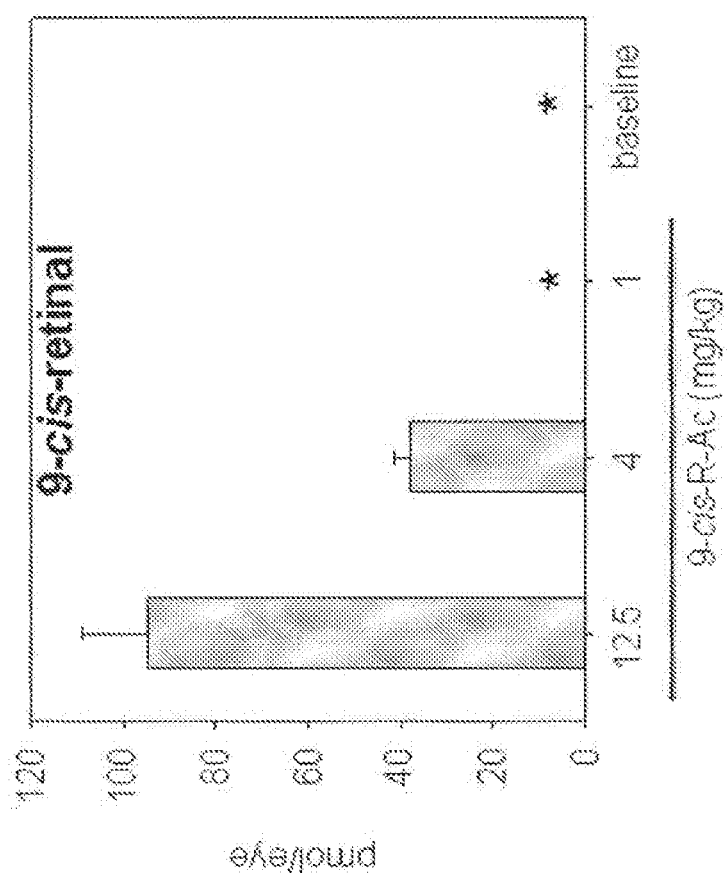
Figures 11A, 11B:
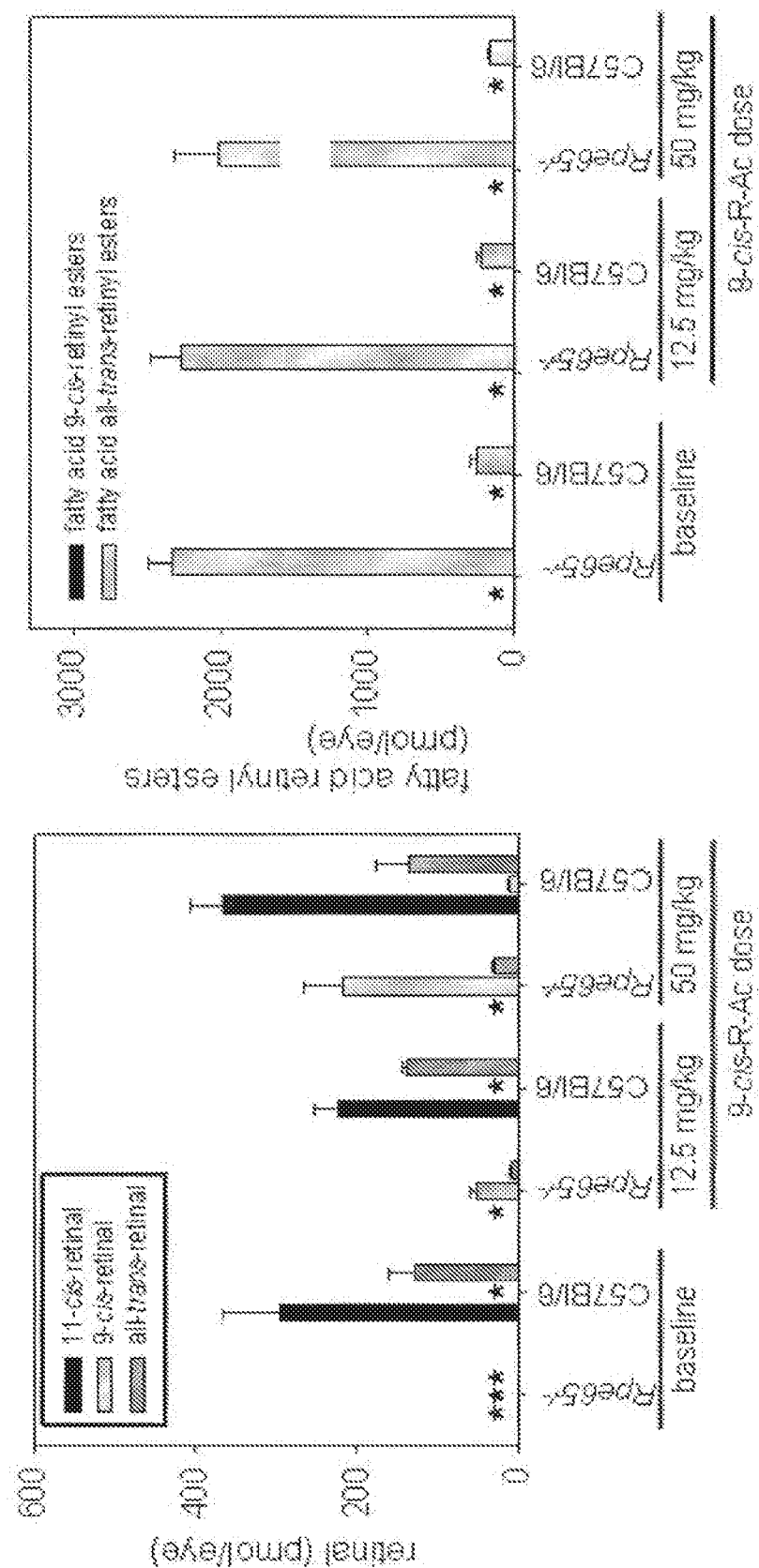
FIG. 11 (A-D) shows the retinoids in the eyes and liver after 14-day daily treatment with 9-cis-retinyl acetate.
Figures 11C, 11D:
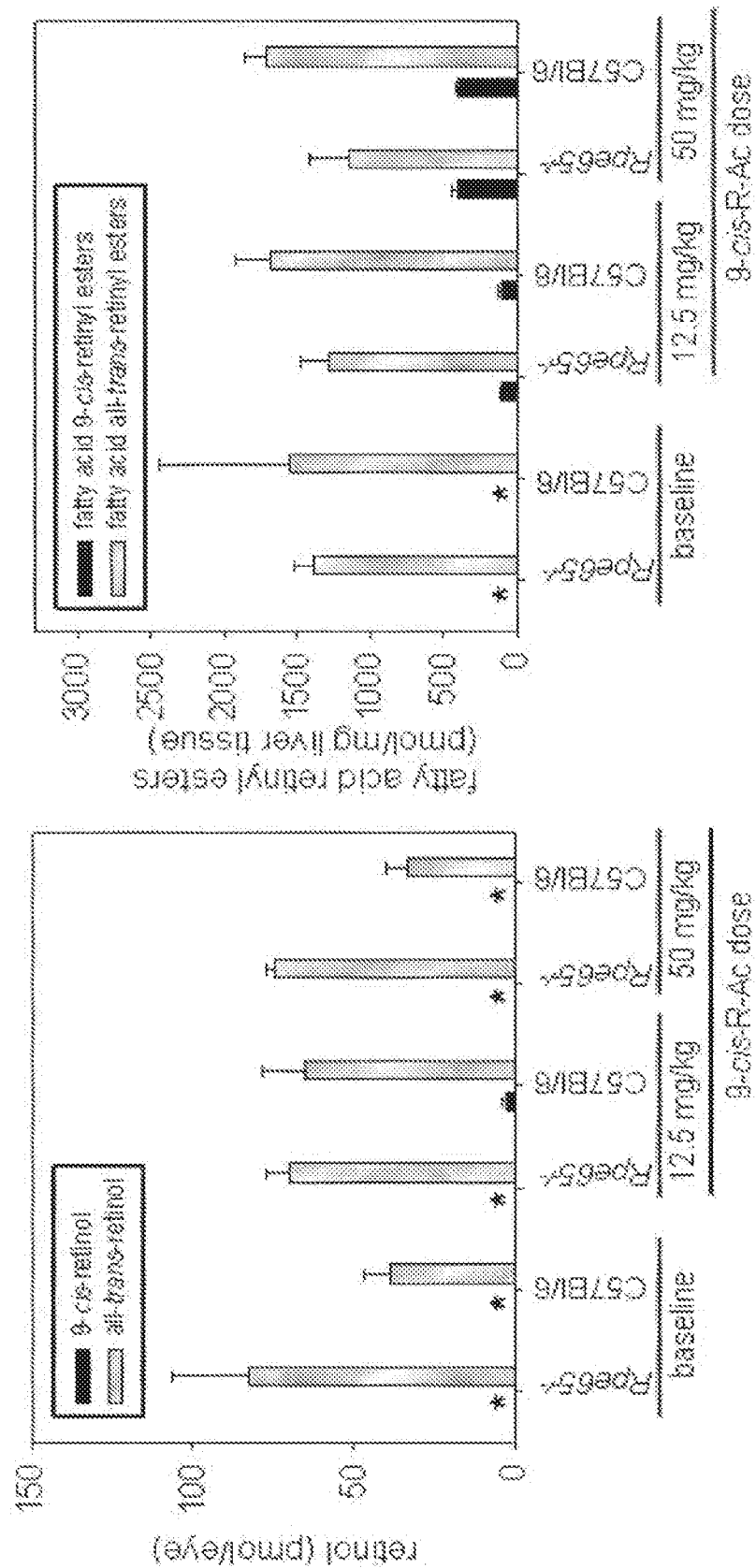

9-cis-Retinal was readily detected in the eyes of the knockout animals but neither fatty acid 9-cis-retinyl esters nor 9-cis-retinol were present (FIG. 11A-C). However, fatty acid 9-cis-retinyl esters did accumulate in a dose-dependent manner in the livers of both C57Bl/6 and Rpe65$^{-/-}$ mice (FIG. 11D). The presence of 9-cis-retinal in the eyes of these mice suggests improvement in retinal function as observed in single dose studies of Rpe65$^{-/-}$ mice. There also was a corresponding dose-dependent accumulation of 9-cis-retinal in the eyes of treated mice (FIG. 4C). No 9-cis-retinal was detected in eyes of the baseline and 1 mg/kg treated groups whereas 38±4 and 95±14 pmol were measured in the daily 4 and 12.5 mg/kg groups, respectively. Levels of fatty acid 9-cis-retinyl esters were low (1 pmol/eye) in the 4 and 12.5 mg/kg/day groups, and undetectable in eyes from other groups (FIG. 4D). Neither all-trans-retinol nor 9-cis-retinol was found in any group. Levels of fatty acid all-trans-retinyl esters (essentially palmitate, stearate and oleate) in the eyes of mice exposed to 9-cis-R-Ac ranged from 1.2 to 1.4 nmol/eye, and were not significantly different from those in control eyes (1.2 nmol/eye at 5-weeks of age).

The ERG responses indicated improved efficacy and kinetics of 9-cis-R-Ac in a dose-dependent manner. The lowest dose (1 mg/kg) significantly improved ERG responses as compared with baseline 5-week-old Rpe65$^{-/-}$ mice even though 9-cis-retinal and fatty acid 9-cis-retinyl esters were not detected in the eye (FIG. 4). This suggests that 9-cis-retinal disappears with light exposure (8 h light/16 h dark) and that fatty acid 9-cis-retinyl esters are utilized to regenerate iso-rhodopsin instead. Indeed, accumulation of fatty acid 9-cis-retinyl esters was detected in liver samples in a dose-dependent manner, which suggests that hepatic stores of fatty acid 9-cis-retinyl esters can serve as a reservoir to generate 9-cis-retinal and iso-rhodopsin in the eye.

The daily dosages of 1, 4, 12.5 and 50 mg/kg were all well tolerated by both 5-week-old C57Bl/6 and Rpe65$^{-/-}$ mice in this 14-day study, signifying the safety of the 9-cis-R-Ac.

Example 5

Duration of Improved Retinal Function after 3 Daily Doses of 9-Cis-R-Ac 9-cis-Retinol in the form of fatty acid 9-cis-retinyl esters accumulated in the liver of Rpe65$^{-/-}$ mice given repeated doses of 9-cis-R-Ac of at least 12.5 mg/kg for 2 weeks (see, FIG. 11D, Example 4).

To assess the capability of mice to store 9-cis-retinoids and later utilize them in the retinoid cycle, 9-cis-R-Ac in soybean oil was gavaged once daily for three consecutive days at a dose of 1, 4, or 12.5 mg/kg/day into 5-week-old Rpe65$^{-/-}$ mice kept in the dark. Mice then were exposed to cycles of 8 h of fluorescent light with luminance range of 500-1500 lux followed by 16 h in the dark.

Figure 5:
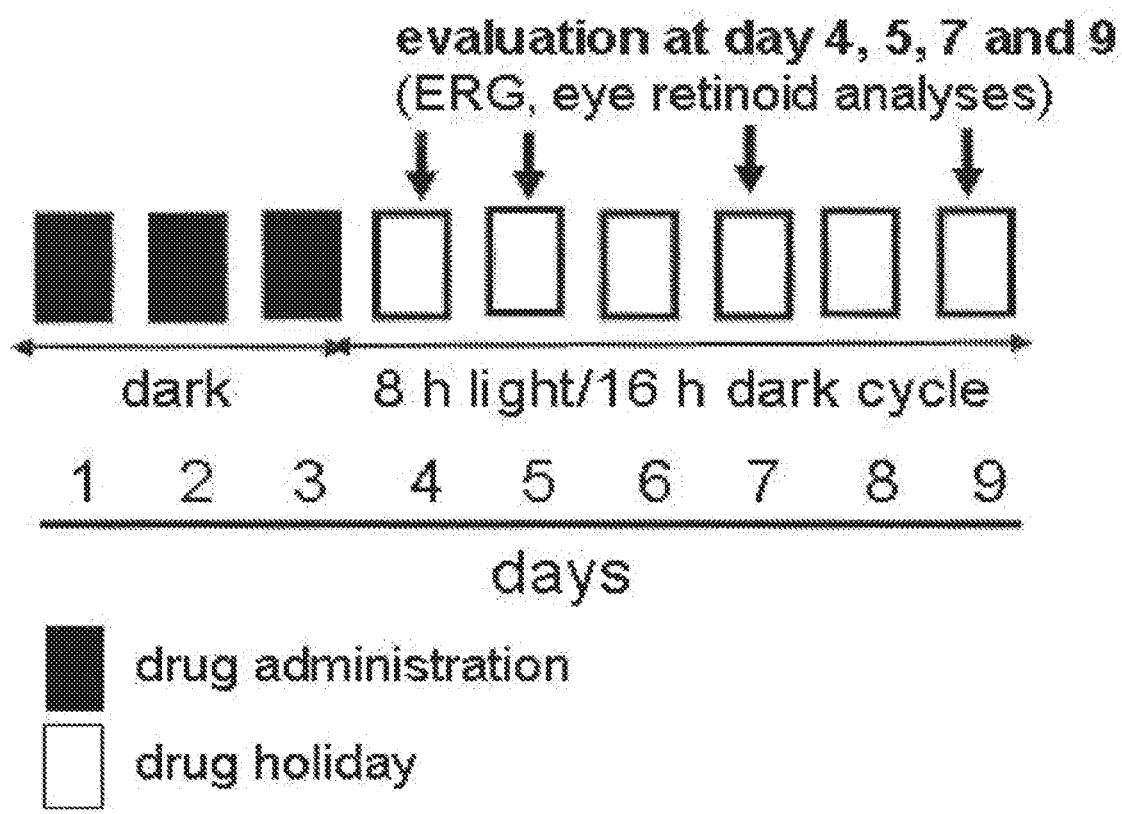
FIG. 5 shows a dosing regimen and evaluation of ERGs and retinoid analyses after three daily doses 9-cis-retinyl acetate in soybean oil.
Figure 6A:
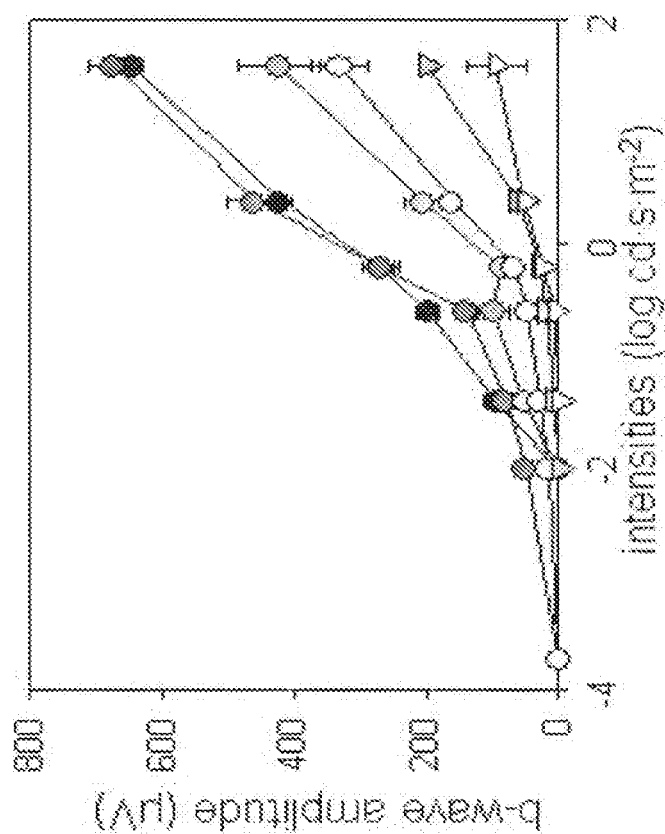
FIG. 6 (A-F) shows dose-dependent a- and b-wave amplitudes of ERG responses recorded up to day 9 after three daily doses of 9-cis-retinyl acetate in soybean oil.
Figure 6B:
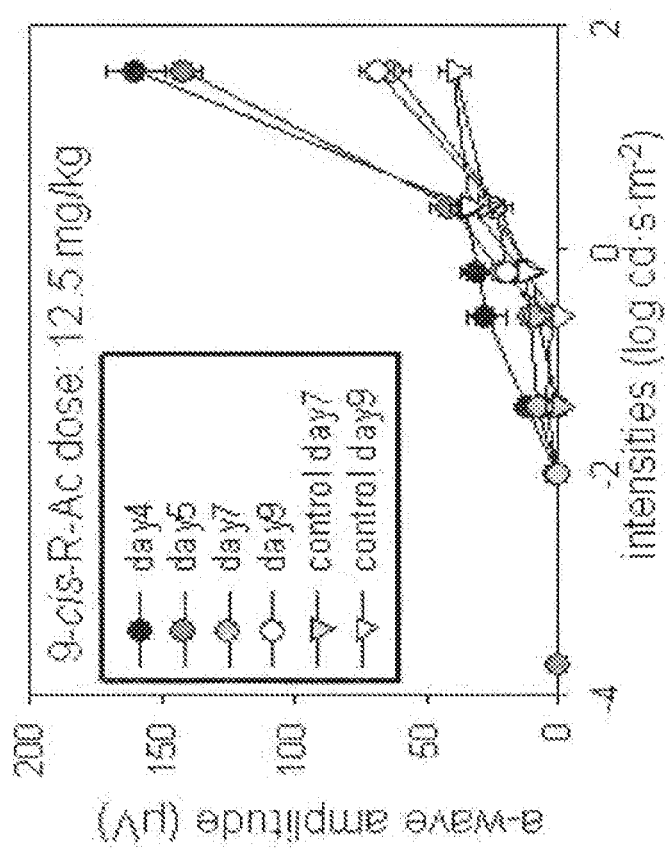
Figure 6D:
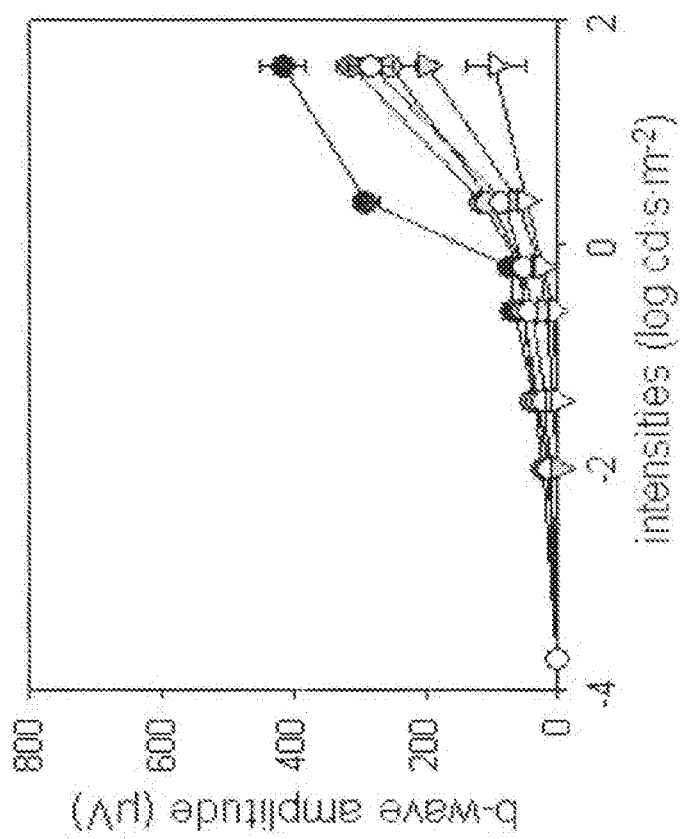
Figure 6C:
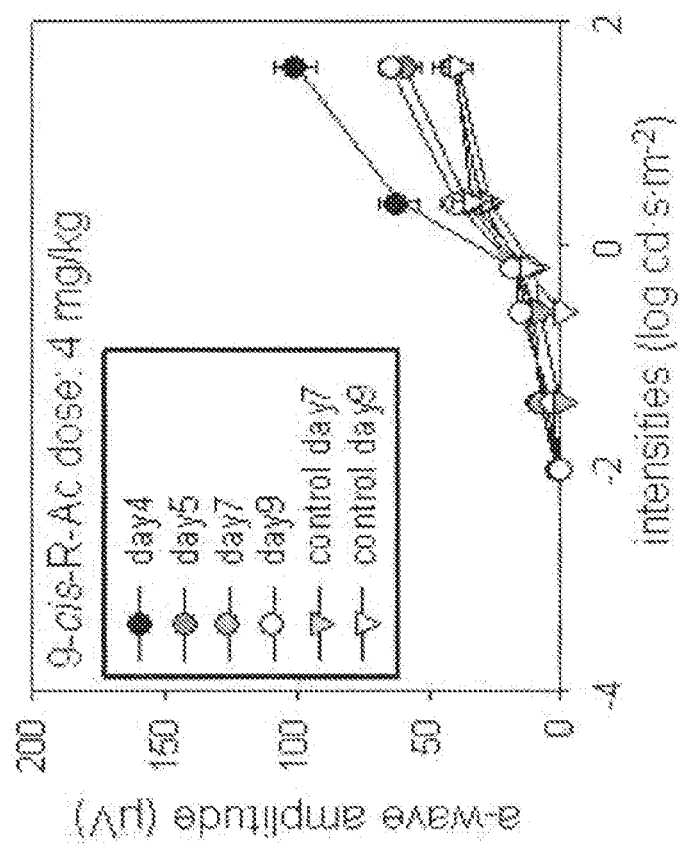
Figure 12:
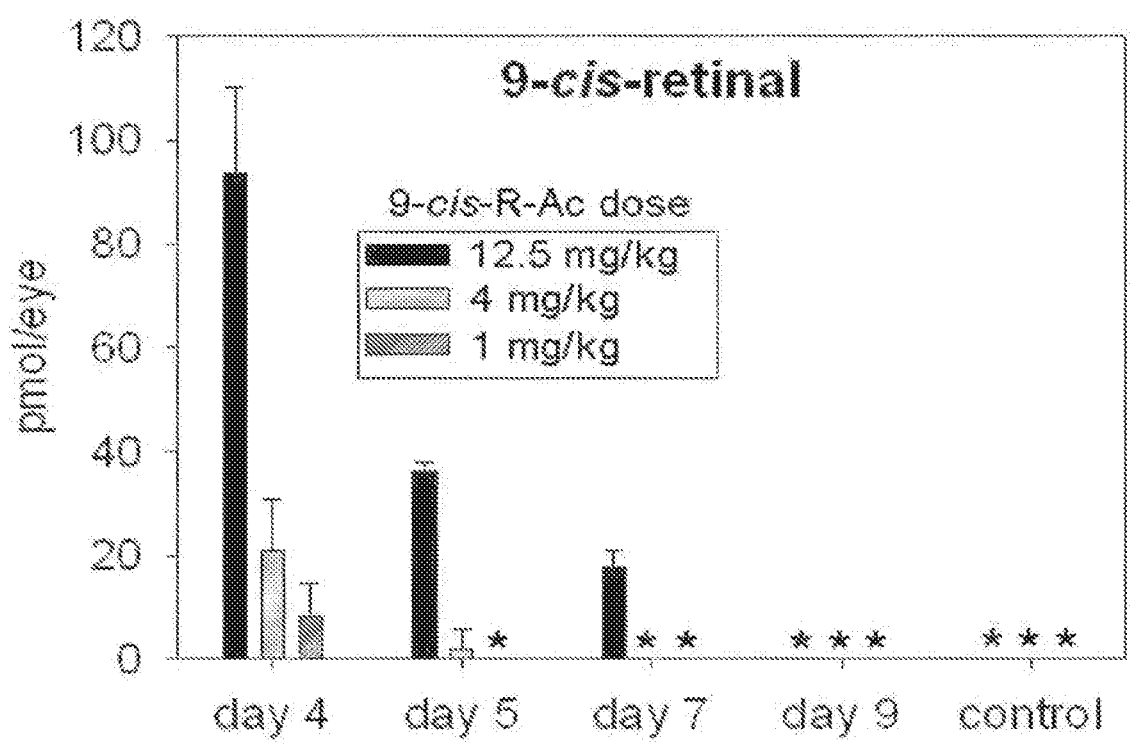
FIG. 12 shows the kinetics of 9-cis-retinal disappearance from the eye after 3 daily doses of 9-cis-retinyl acetate.

ERGs and retinoid analyses were performed at the end of the first (day 4), second (day 5), fourth (day 7), and sixth (day 9) days of light exposure (FIG. 5). Both a- and b-wave amplitudes of ERG responses recorded up to day 9 (FIG. 6A-F) were dose-dependent at each time point and declined with the number of light exposures. The highest tested dose (12.5 mg/kg/day) significantly improved both a- and b-waves up to day 9 (FIG. 6A-B) at high intensity stimuli, whereas doses of 4 mg/kg and 1 mg/kg showed improvement in a-wave amplitudes up to day 9 and day 7, respectively, and in b-wave amplitudes up to day 9 (FIG. 6C-F). Levels of 9-cis-retinal in the eye also were dose-dependent and decreased over time (FIG. 12). This compound was detected in the retinas of all treated mice at day 4 (FIG. 12), but only in the retinas of mice exposed to 4 and 12.5 mg/kg at day 5, and only in the 12.5 mg/kg group at day 7. No 9-cis-retinal was found in the retinas of treated or control mice by day 9. Thus, daily administration of 9-cis-R-Ac was not needed to deliver 9cis-R-Ac to the eye and sustain improvement in retinal function of Rpe65$^{-/-}$ mice.

Thus, it is shown that the ERG amplitudes improved in a generally dose-dependent manner and this positive effect was maintained for up to 4-6 days after treatment. Moreover, a similar pattern was noted for 9-cis-retinal levels found in the eyes of these animals. Importantly, improvement of ERG responses at the 4 mg/kg dose level lasted for 4-6 days after cessation of treatment when 9-cis-retinal could no longer be found in the eyes. These results indicate that the positive effects of 9-cis-R-Ac therapy are retained by trace levels of 9-cis-retinal in the retina that stabilize the ROS, whereas ERG responses in the control groups had deteriorated. The kinetics of retinoid levels in eyes then were examined during dark-adaptation after light exposure. Importantly, restoration of fatty add 9-cis-retinyl esters and 9-cis-retinal in the eyes occurred during dark-adaptation.

Example 6

Retinal Function of Rpe65$^{-/-}$ Mice after Intermittent and Daily Administration of 9-Cis-R-Ac for 8 Weeks Because 3 low daily doses of 9-cis-R-Ac improved ERG responses after 6 days of light exposure (FIG. 6A-F), a prolonged 8-week intermittent dosing regimen was carried out.

Figure 7:
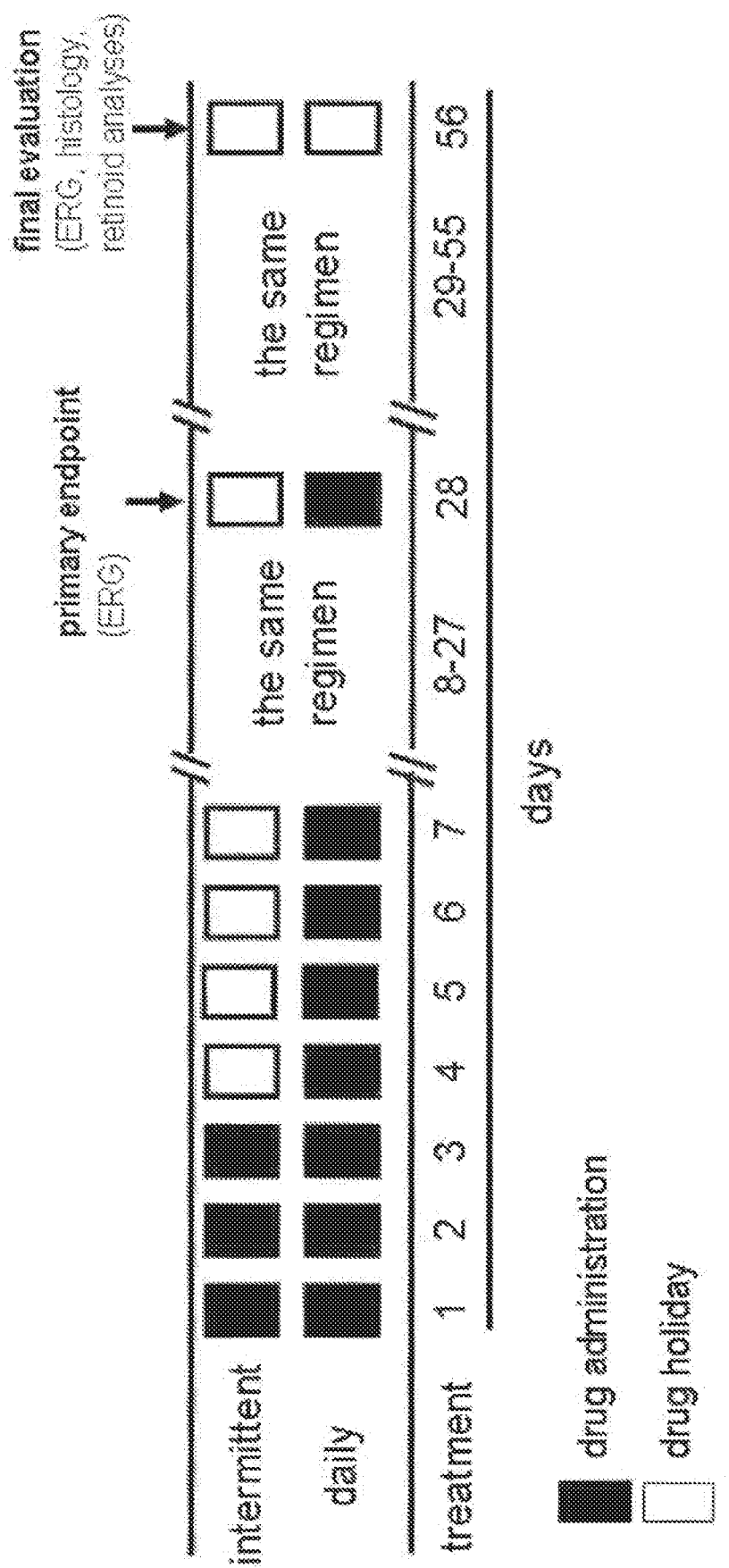
FIG. 7 shows an intermittent dosing regimen and a daily dosing regimen during an 8-week period.

Rpe65$^{-/-}$ mice were split into two groups (an intermittent group and a daily group), each treated for a total of 8 weeks with 1 or 4 mg/kg of 9-cis-R-Ac. The intermittent group was dosed daily for 3 days followed by a 4-day drug holiday during each week of the 8-week regimen. The daily group was dosed daily for the entire 8-week period. The dosing regimens are illustrated in FIG. 7. Mice were exposed to a daily cycle of 8 h of fluorescent light with luminance range of 500-1500 lux followed by 16 h darkness. ERGs were recorded at day 28 and again at day 56, after which tissues were collected for retinoid analyses of the eye and liver and histology of the eye.

Figures 8A, 8B:
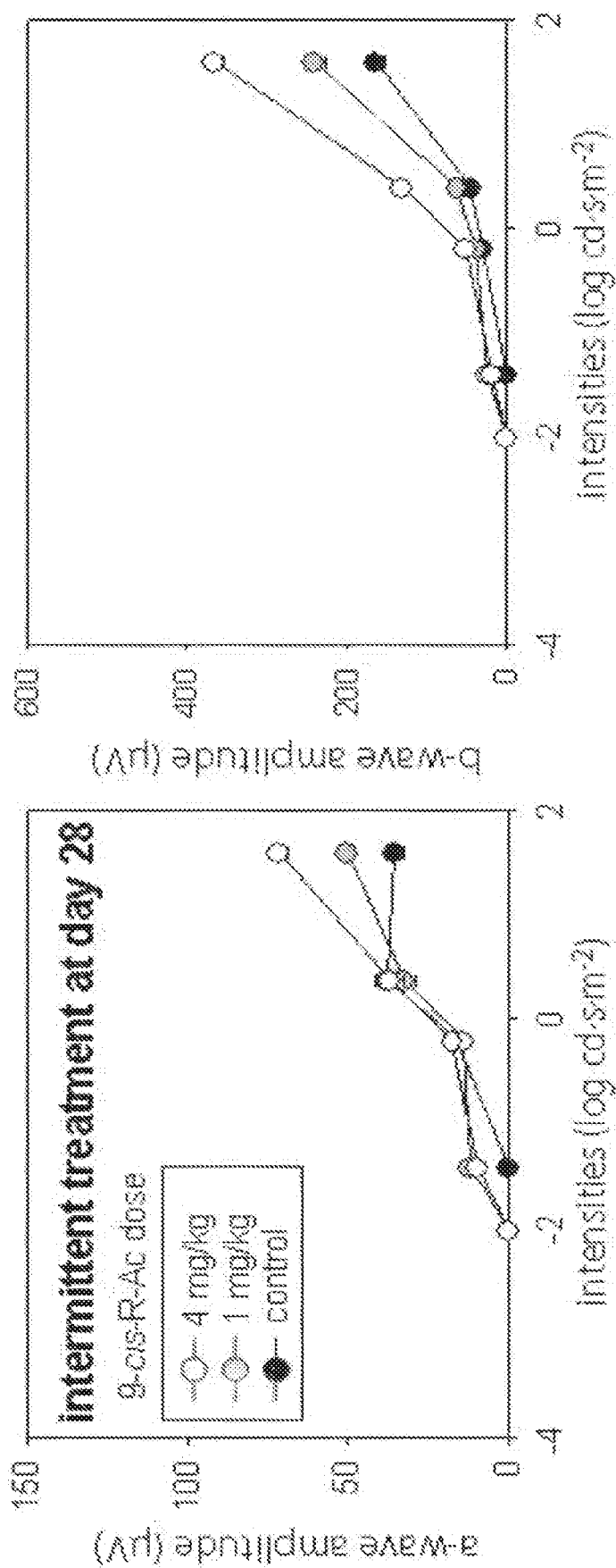
FIG. 8 (A-D) shows a dose-dependent increase in the amplitude of a- and b-waves on days 28 and 56 in the intermittent dosing regimen and daily dosing regimen.
Figure 8D:
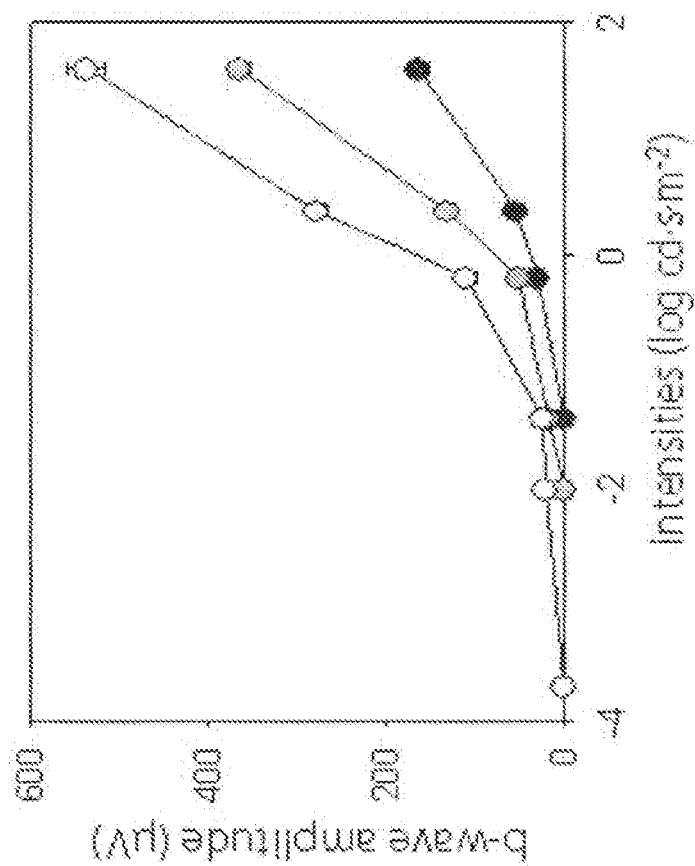
Figure 8C:
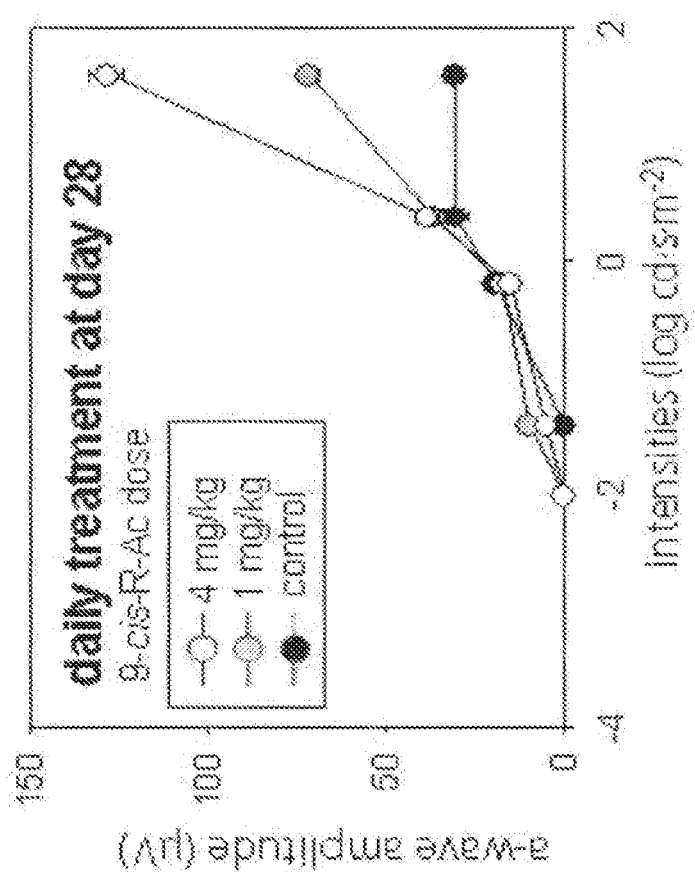
Figure 9B:
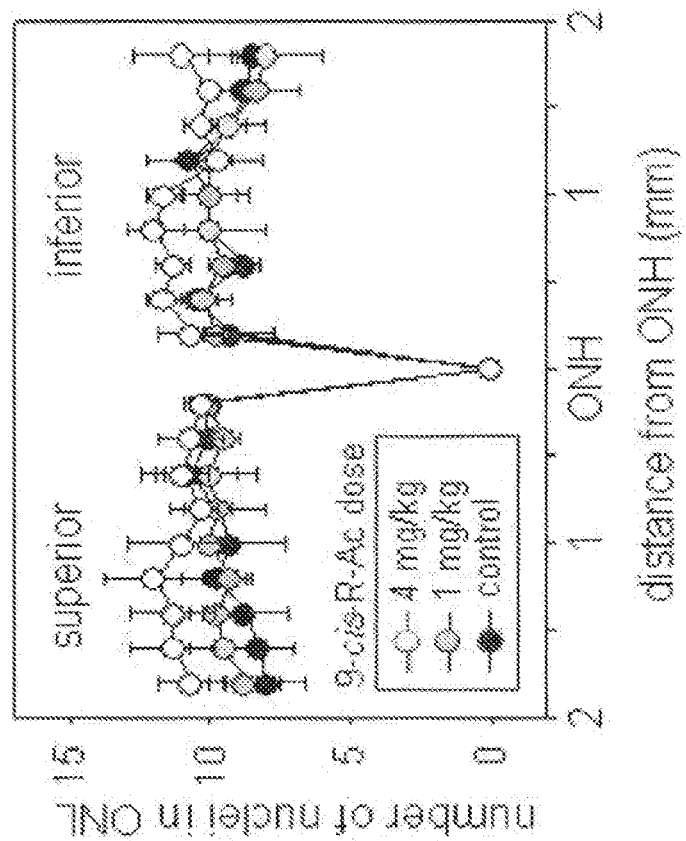
FIG. 9 (A-I) shows, following a long term administration of 9-cis-retinyl acetate, a dose-dependent protective effect on the retina as assessed by the lengths of the photoreceptor outer segments.
Figure 9A:
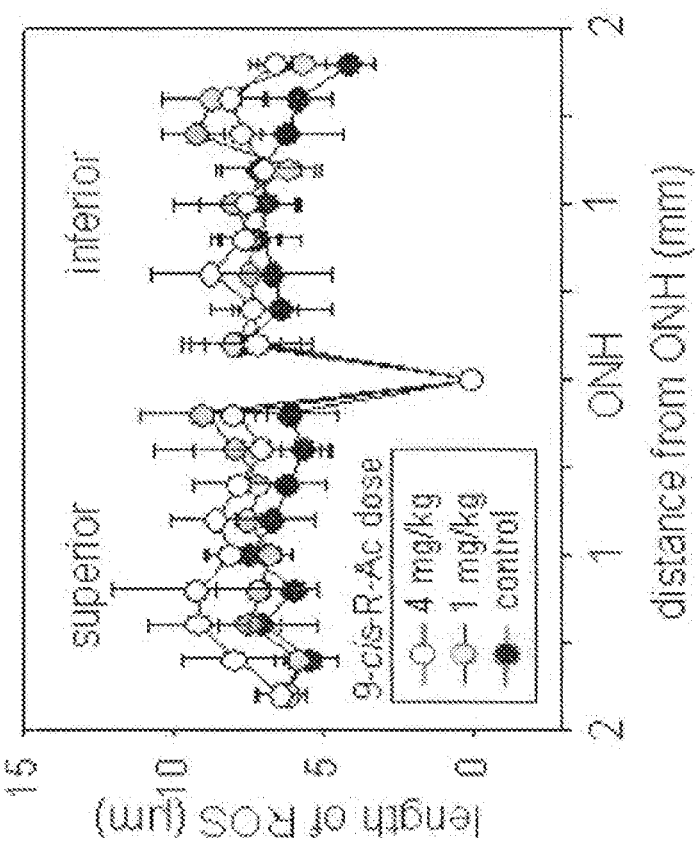
Figure 9D:
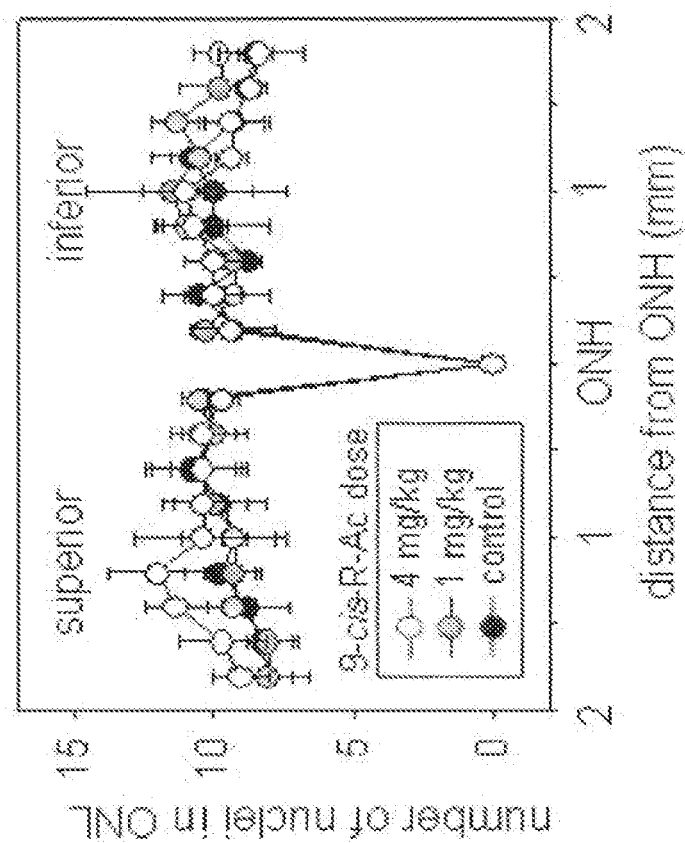
Figure 9C:
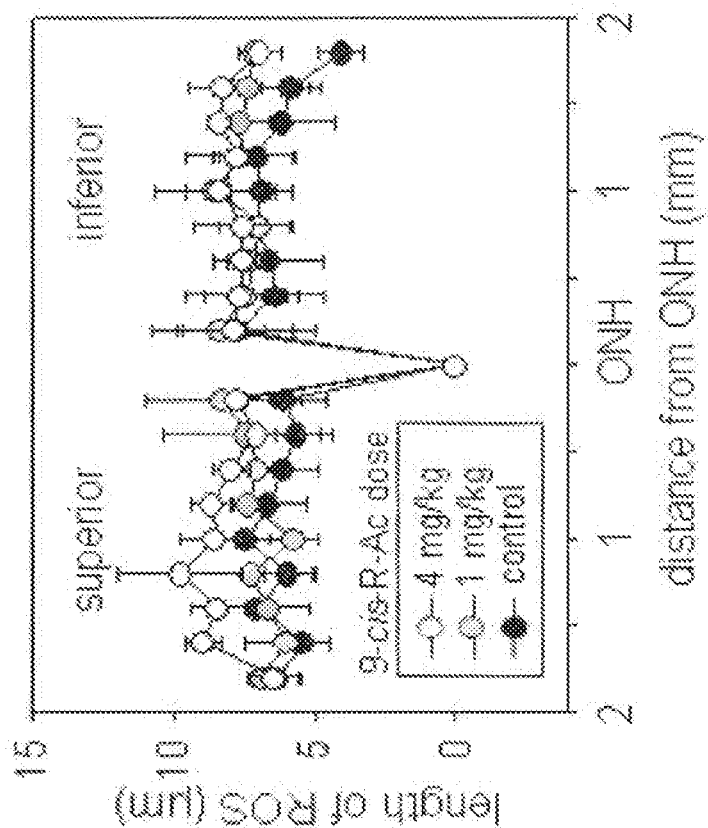
Figure 9E:
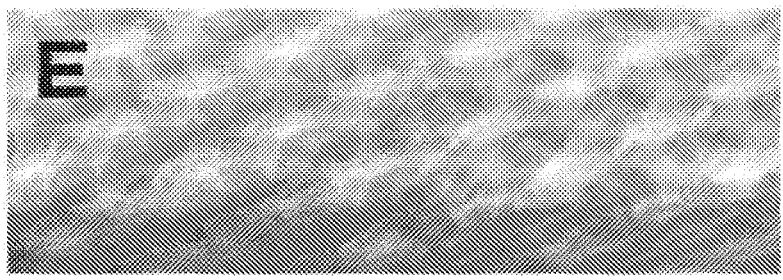
Figure 9F:
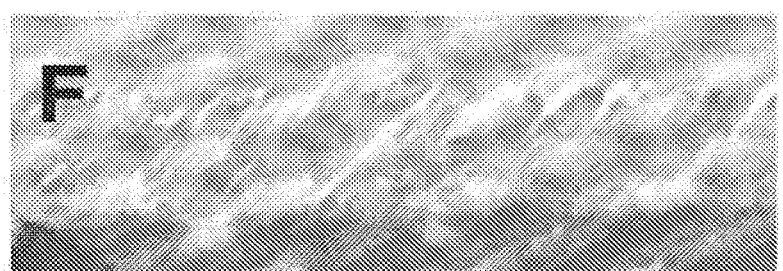
Figure 9G:
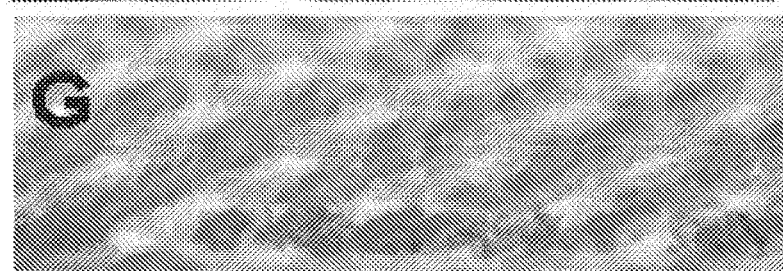
Figure 9H:
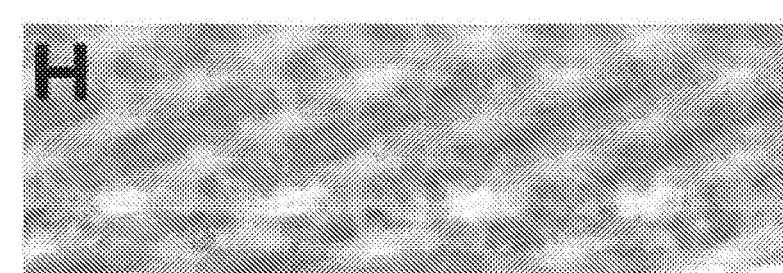
Figure 9I:
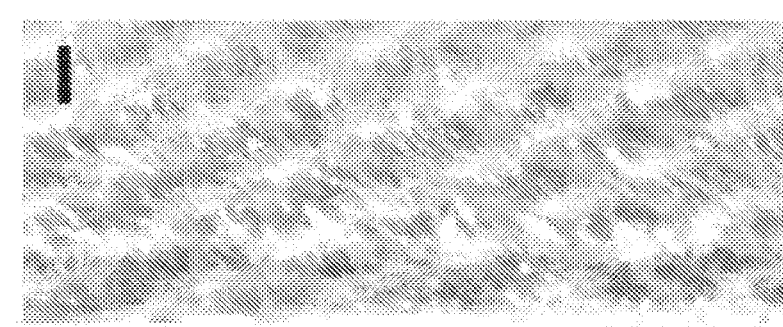
Figures 13A, 13B:
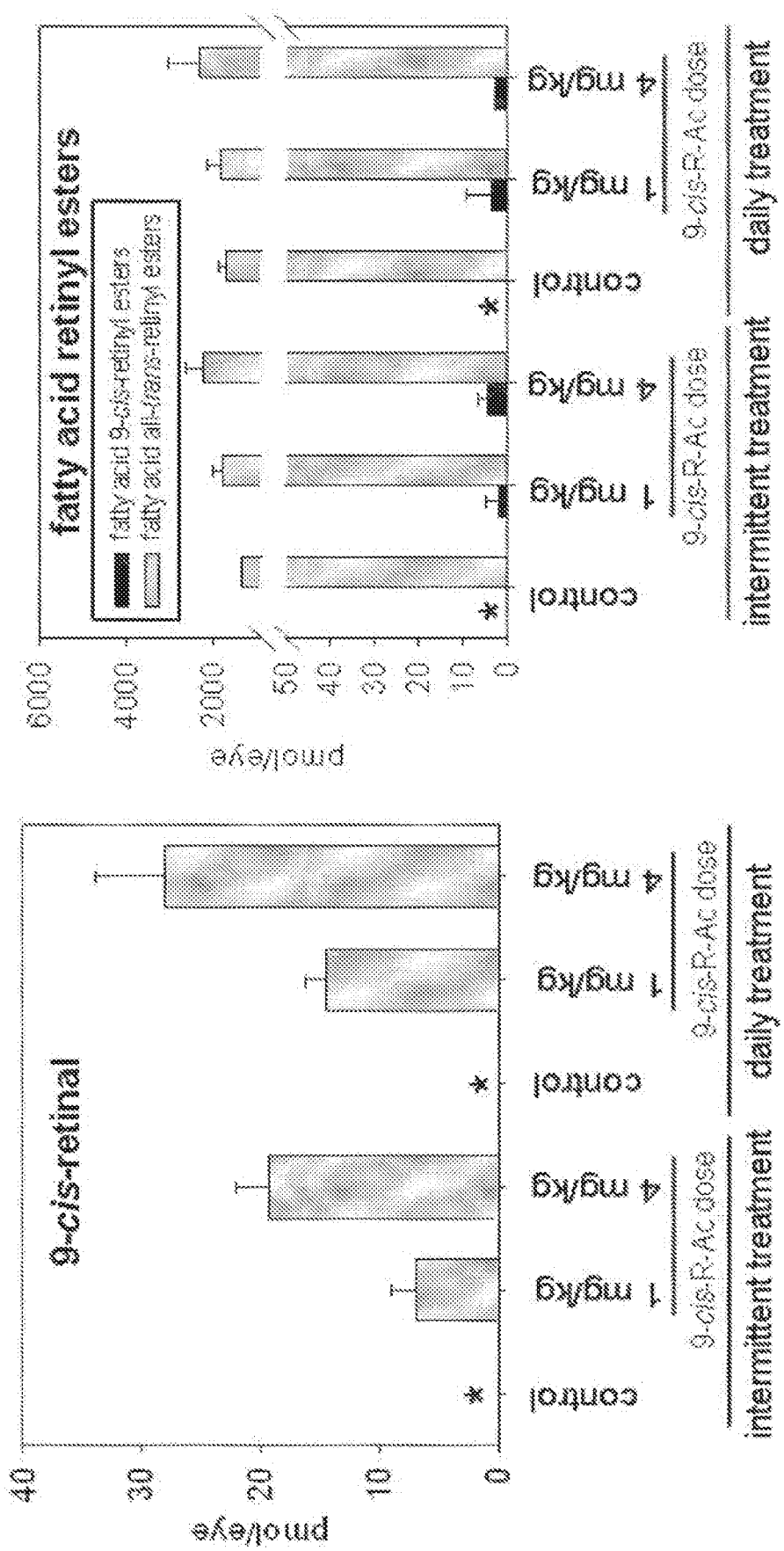
FIG. 13 (A-B) shows the retinoid content in the eyes of Rpe65−/− mice after intermittent and daily treated with 9-cis-R-Ac for 8 weeks.
Figure 14A:
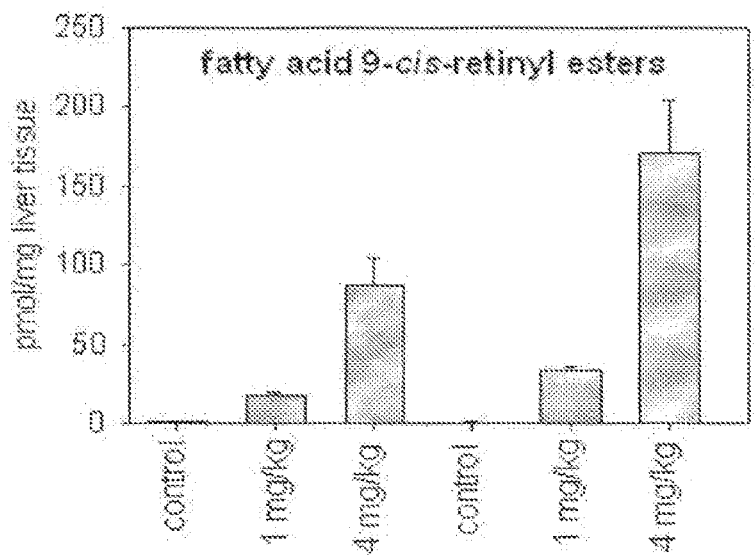
FIG. 14 (A-C) shows the retinoid analyses in livers of Rpe65−/− mice after 56-day intermittent and daily treatment with 9-cis-retinyl acetate.
Figure 14B:
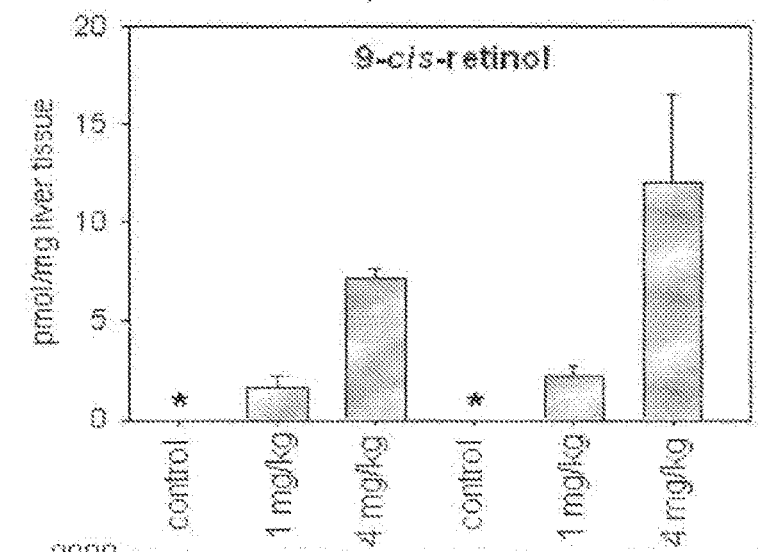
Figure 14C:
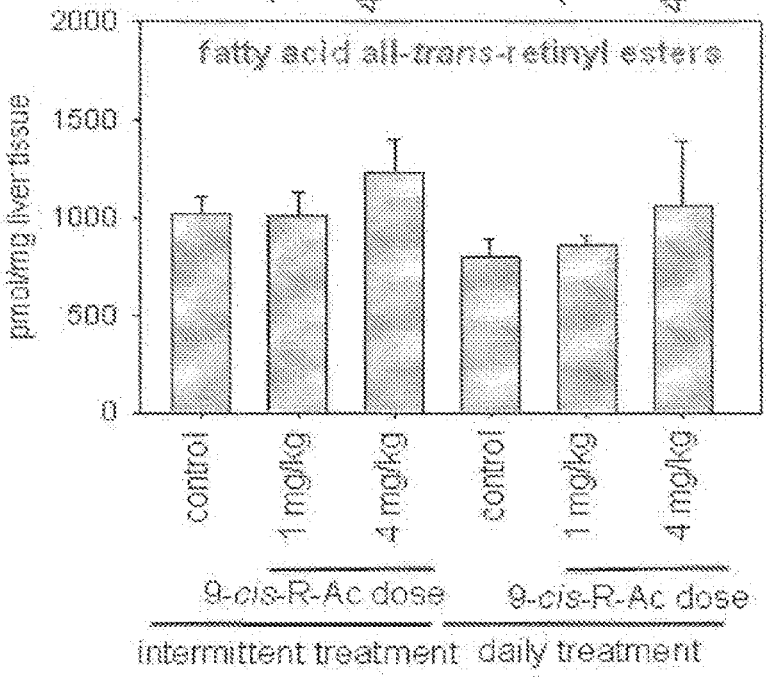

ERG responses of treated mice in intermittent group and daily group were significantly better than those of controls at both day 28 and day 56, and mild tapering of amplitudes between day 28 and day 56 was noted in both the 9-cis-R-Ac treated mice and control mice. Both the intermittent dosing and daily dosing regimens evoked a dose-dependent increase in the amplitude of a- and b-waves on days 28 and 56 (FIG. 8A-D). Responses were more pronounced in the daily dosed than in the intermittently dosed group. The lower dose (1 mg/kg) was sufficient to cause a significant improvement in ERG responses over the control group at high intensity stimuli, irrespective of the treatment schedule. In addition, the amplitudes of the a- and b-waves were similar at day 28 and 56, suggesting that equilibrium may have been achieved between the intake and storage of 9-cis-retinol on one hand and its mobilization in the retina to support the retinoid cycle on the other. In agreement with these ERG results, 9-cis-retinal was detected in a dose-dependent manner in the eyes where levels were higher in mice dosed daily (FIG. 13A). Fatty acid 9-cis-retinyl esters at low variable levels also were found in the eyes of both sets of treated animals (FIG. 13B). A dose-dependent slight increase in fatty acid all-trans-retinyl esters also was noted in the eyes of treated mice regardless of the regimen. In the liver, 9-cis-retinol was essentially stored in the form of fatty acid 9-cis-retinyl esters in a dose and regimen-dependent manner (FIG. 14A, B). Levels of fatty acid all-trans-retinyl esters were not significantly affected by these regimens, although there may have been a slight increase in mice receiving 4 mg/kg 9-cis-R-Ac. Long term administration of 9-cis-R-Ac had a dose-dependent protective effect on the retina as assessed by the lengths of the photoreceptor outer segments (FIG. 9A, C) and number of nuclei in the outer nuclear layer (FIG. 9B, D). These effects were more pronounced in the superior than inferior retina. More highly magnified images of retinal cross sections showed improvement of rod outer segment (ROS) morphology and fewer oil droplet-like structures in parts of the superior and inferior portions of retinas from mice treated with either the 4 mg/kg daily or 4 mg/kg intermittent regimens (FIG. 8E, F). However, no significant change was observed in retinas of mice receiving the 1 mg/kg 9-cis-R-Ac dose by either schedule (FIG. 9G, H) as compared with retinas of control mice (FIG. 9I).

Importantly, ERG responses of mice treated intermittently with 9-cis-R-Ac evidenced no significant difference between the 1 and 4 mg/kg dose groups at day 56, suggesting that the lower 1 mg/kg dose may have similar efficacy if given continuously. As shown in FIG. 9, morphological improvements of ROS were observed such that ROS lengths were significantly longer in the superior retina of mice treated with 4 mg/kg whereas no significant changes were noted in animals given the 1 mg/kg dose. From these observations, it is strongly suggested that treatment regimens of both 1 and 4 mg/kg maintained retinal function in Rpe65$^{-/-}$ mice without significant clinical toxicity or abnormal retinoid accumulation in the eyes and liver.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A liquid oral pharmaceutical formulation suitable for treating a human subject with an endogenous 11-cis-retinal deficiency consisting essentially of 9-cis-retinyl acetate in soybean oil and an anti-oxidant, wherein the soybean oil is U.S.P. grade soybean oil.

2. The formulation of claim 1, wherein said formulation is not in the form of a capsule.

3. The formulation of claim 1, wherein the 9-cis-retinyl acetate is present up to 30% by weight of the formulation.

4. The formulation of claim 1, wherein the 9-cis-retinyl acetate is present up to 25% by weight of the formulation.

5. The formulation of claim 1, wherein the 9-cis-retinyl acetate is present up to 10% by weight of the formulation.

6. The formulation of claim 1, wherein the 9-cis-retinyl acetate is present up to 5% by weight of the formulation.

7. The formulation of claim 1, wherein the 9-cis-retinyl acetate is present from about 1.25 to 20 mg/mL in the formulation.

8. The formulation of claim 1, wherein the 9-cis-retinyl acetate is present at about 20 mg/mL in the formulation.

9. The formulation of claim 1, wherein the anti-oxidant comprises a-tocopherol, butylated hydroxyanisole (BHA), butylated hydroxytoluene (BHT), ascorbyl palmitate, propyl gallate, tert-butyl hydroquinone (TBHQ), or a chelating agent, or a combination thereof.

10. The formulation of claim 1, wherein the anti-oxidant comprises butylated hydroxyanisole (BHA).

11. The formulation of claim 1, wherein the formulation comprises about 0.1% by weight to volume of the anti-oxidant.

12. The formulation of claim 1, wherein the 11-cis-retinal deficiency is due to an RPE65 mutation.

13. The formulation of claim 1, wherein the 11-cis-retinal deficiency is due to an LRAT mutation.

14. The formulation of claim 1, wherein the human subject has Leber congenital amaurosis (LCA).

15. The formulation of claim 1, wherein the human subject has Retinitis Pigmentosa (RP).

16. The formulation of claim 1, wherein the formulation is configured to provide a dosage of about 1.25-40 mg/m$^2$ of the 9-cis-retinyl acetate by body surface area to the subject.

17. The formulation of claim 1, wherein the formulation is configured to provide a dosage of about 40 mg/m$^2$ of the 9-cis-retinyl acetate by body surface area to the subject.

18. The formulation of claim 1, wherein the formulation is in the form of an oil-in-water emulsion.

19. The formulation of claim 1, wherein the formulation is configured for single dosing, intermittent dosing or daily dosing.

20. The formulation of claim 1, wherein the formulation is packaged in an amber container.

* * * * *